(12) United States Patent
Burrell

(10) Patent No.: US 12,061,195 B2
(45) Date of Patent: Aug. 13, 2024

(54) ALUMINUM OXIDE SURFACES AND INTERFACE MOLECULES

(71) Applicant: Pavonis Diagnostics Inc., Edmonton (CA)

(72) Inventor: Robert Edward Burrell, Sherwood Park (CA)

(73) Assignee: Pavonis Diagnostics Inc., Edmonton (CA)

(*) Notice: Subject to any disclaimer, the term of this patent is extended or adjusted under 35 U.S.C. 154(b) by 957 days.

(21) Appl. No.: 16/971,284

(22) PCT Filed: Feb. 20, 2019

(86) PCT No.: PCT/CA2019/050204
§ 371 (c)(1),
(2) Date: Aug. 19, 2020

(87) PCT Pub. No.: WO2019/161491
PCT Pub. Date: Aug. 29, 2019

(65) Prior Publication Data
US 2022/0205994 A1  Jun. 30, 2022

Related U.S. Application Data

(60) Provisional application No. 62/633,009, filed on Feb. 20, 2018.

(51) Int. Cl.
*G01N 33/543* (2006.01)
*G01N 33/553* (2006.01)

(52) U.S. Cl.
CPC ..... *G01N 33/54353* (2013.01); *G01N 33/553* (2013.01)

(58) Field of Classification Search
None
See application file for complete search history.

(56) References Cited

U.S. PATENT DOCUMENTS

| | | |
|---|---|---|
| 4,769,320 A | 9/1988 | Furie et al. |
| 4,808,530 A | 2/1989 | Means et al. |
| 5,124,172 A | 6/1992 | Burrell et al. |
| 5,468,606 A | 11/1995 | Bogart et al. |
| 6,060,237 A | 5/2000 | Nygren et al. |
| 6,225,131 B1 | 5/2001 | van Damme et al. |
| 6,596,545 B1 | 6/2003 | Wagner et al. |
| 6,589,799 B2 | 7/2003 | Coyne et al. |
| 6,951,690 B2 | 10/2005 | Katz et al. |
| 7,045,365 B2 | 5/2006 | Coyne et al. |
| 7,622,263 B2 | 11/2009 | Ban et al. |
| 8,063,018 B2 | 11/2011 | Ni et al. |
| 8,110,349 B2 | 2/2012 | Cohen et al. |
| 8,178,602 B2 | 5/2012 | Mao et al. |
| 8,920,725 B2 | 12/2014 | Withrow et al. |
| 9,011,870 B2 | 4/2015 | Leenhouts et al. |
| 9,212,365 B2 | 12/2015 | Perret et al. |
| 9,618,510 B2 | 4/2017 | Aghvanyan et al. |
| 9,694,048 B2 | 7/2017 | Bauzon et al. |
| 9,709,563 B2 | 7/2017 | Hobbs |
| 2002/0106702 A1 | 8/2002 | Wagner et al. |
| 2006/0228813 A1 | 10/2006 | Wu et al. |
| 2012/0040905 A1 | 2/2012 | Perret et al. |
| 2014/0030822 A1 | 1/2014 | Hataoka |
| 2014/0363833 A1 | 12/2014 | Bhatia et al. |

FOREIGN PATENT DOCUMENTS

WO  WO 2006/104035 A1  10/2006
WO  WO 2012/168988 A1  12/2012

OTHER PUBLICATIONS

Abd-Elnaiem et al. (2013) "Parametric study on the anodization of pure aluminum thin film used in fabricating nano-pores template," International Journal of Electrochemical Science, vol. 8, No. 7, pp. 9741-9751.
Alvarez et al. (2009) "A label-free porous alumina interferometric immunosensor," ACS Nano, vol. 3, No. 10, pp. 3301-3307.
Amphlett et al. (1978) "The binding of metal ions to bovine factor IX," The Journal of Biological Chemistry, 253(19), pp. 6774-6779.
Aramesh et al. (2014) "Surface Modification of Porous Anodic Alumina for Medical and Biological Applications," Nanomedicine Isbn (Ebook), One Central Press (OCP), pp. 439-467.
Araoyinbo et al. (2010) "A novel process to produce nanoporous aluminum oxide using titration technique to prepare the neutral electrolyte," Journal of Non-Crystalline Solids, vol. 356, pp. 1057-1060.
Bajaj et al. (1975) "Prothrombin fragments. Ca2+ binding and activation kinetics," The Journal of Biological Chemistry, 250(6), pp. 2150-2156.
Belwalkar et al. (2008) "Effect of processing parameters on pore structure and thickness of anodic aluminum oxide (AAO) tubular membranes," Journal of Membrane Science 319, pp. 192-198.
Bowen et al. (1992) "Properties of Microfiltration Membranes: The Effects of Adsorption and Shear on the Recovery of an Enzyme," Biotechnology and Bioengineering, 40, pp. 491-497.

(Continued)

*Primary Examiner* — Stacy B Chen
(74) *Attorney, Agent, or Firm* — Leydig, Voit & Mayer, Ltd.

(57) ABSTRACT

A device, interface complex, diagnostic system, kit or method for use in binding analyte of interest, wherein immobilizing is on an aluminum oxide surface. An interface molecule is immobilized on the aluminum oxide surface. Attached to the interface molecule, is a cross linking agent for binding to the analyte, or a biomolecule specific to the analyte. The interface molecule includes a polypeptide having at least one carboxy rich domain providing at least 5 free carboxyl groups within a molecular volume of 2.2-25 $nm^3$, the free carboxyl groups being provided by amino acids containing two or more carboxyl groups, through which the interface molecule is immobilized to the aluminum oxide surface. The biomolecule may be covalently attached to the interface molecule, or the biomolecule may bean engineered antibody attached to the interface molecule through an antigenic determinant or through an Fc fragment.

22 Claims, 22 Drawing Sheets
Specification includes a Sequence Listing.

(56) References Cited

OTHER PUBLICATIONS

Brinkmann et al. (Jan. 2017) "The making of bispecific antibodies," MABS, 9, 2, 182-212 http://dx.doe.org/10.1080/19420862.2016.1268307.
Delaney et al. (2009) "Inkjet printing of proteins," Soft Matter, 5, pp. 4866-4877, DOI:10.1039/b909878j.
Djokic et al. (1998) "Visual detection of protein adsorption onto electrochemically oxidized aluminum surfaces," Biosensors and Bioelectronics, vol. 13, No. 3-4, pp. 271-278.
Extended European Search Report dated Oct. 5, 2021 in EP Application No. 19757889.1, 10 pp.
Furie et al. (1979) "Metal binding sites of a gamma-carboxyglutamic acid-rich fragment of bovine prothrombin," The Journal of Biological Chemistry, 254(24), pp. 12521-12530.
Furie et al. (1988) "The molecular basis of blood coagulation," Cell, 53, pp. 505-518.
Hyndman et al. (1992) "Protein Immobilization to Alumina Supports: I. Characterization of Alumina-Organophosphate Ligand Interactions and Use in the Attachment of Papain," Biotechnology and Bioengineering, vol. 40, pp. 1319-1327.
Hyndman et al. (1992) "Protein Immobilization to Alumina Supports: II. Papain Immobilization to Alumina via Organophosphate Linkers," Biotechnology and Bioengineering, vol. 40, pp. 1328-1336.
International Preliminary Report on Patentability mailed Sep. 3, 2020, in corresponding PCT/CA2019/050204, 8 pp.
Kotkow et al. (1993) "The interaction of prothrombin with phospholipid membranes is independent of either kringle domain," The Journal of Biological Chemistry, 268(21), pp. 15633-15639.
Li et al. (1998) "On the growth of highly ordered pores in anodized aluminum oxide," Chemistry of Materials, vol. 10, No. 9, pp. 2470-2480.
Li et al. (2015) "Inkjet printing for biosensor fabrication; combining chemistry and technology for advanced manufacturing," Lab Chip, 15, pp. 2538-2558 DOI: 10.1039/c51c00235d.
Liu et al. (Jan. 2017) "Fc Engineering for Developing Therapeutic Bispecific Antibodies and Novel Scaffolds," Frontiers in Immunology 8: 38, 15 pages.
Lundwall et al. (1986) "Isolation and sequence of the cDNA for human protein S, a regulator of blood coagulation," Proc. Natl. Acad. Sci. USA, 83, pp. 6716-6720.
Macias et al. (2015) "Effect of pore diameter in nanoporous anodic alumina optical biosensors," Analyst, vol. 140, No. 14, 4848-4854.
Mann (1976) "Prothrombin," Methods in Enzymology, vol. 45 (pt. B), pp. 123-156.
McWilliam et al. (2011) "Inkjet printing for the production of protein microarrays," *Protein Microarrays: Methods and Protocols*, Methods in Molecular Biology, vol. 785, pp. 345-351 DOI:10.1007/978-1-61779-286-1_23.
Murray (1980) "Physical Chemistry of Virus Adsorption and Degradation on Inorganic Surfaces: Its relation to wastewater treatment," United States Environmental Protection Agency, 84 pages.
Murray et al. (1979) "Degradation of Poliovirus by Adsorption on Inorganic Surfaces," Applied and Environmental Microbiology, 37(3), pp. 480-486.
Nelsestuen et al. (1978) "Interaction of vitamin K dependent proteins with membranes," Biochemistry, 17(11), pp. 2134-2138.
Ono et al. (2003) "Evaluation of pore diameter of anodic porous films formed on aluminum," Surface and Coatings Technology, vol. 169-170, pp. 139-142.
Rahman et al. (2012) "Effect of the anodization voltage on the pore-widening rate of nanoporous anodic alumina," Nanoscale Research Letters, 7:474, 7 pp.
Ratcliffe et al. (1993) "The importance of specific γ-carboxyglutamic acid residues in prothrombin," J. Biol. Chem. vol. 268, No. 32, pp. 24339-24345.
Singh et al. (2014) "Highly ordered anodic porous alumina membrane and surface modification approaches for biomedical application," J. App. Chem., vol. 7, pp. 17-34.
Sugo et al. (1986) "Calcium binding of bovine protein S. effect of thrombin cleavage and removal of the gamma-carboxyglutamic acid-containing region," The Journal of Biological Chemistry, 261(11), pp. 5116-5120.
Sumarheni et al. (2014) "Human Full-Length Coagulation Factor X and a GLA Domain-Derived 40-mer Polypeptide Bind to Different Regions of the Adenovirus Serotype 5 Hexon Capsomer," Human Gene Therapy, vol. 25, No. 4, pp. 339-349.
Thermo Scientific (2012) "Crosslinking Technical Handbook," 56 pp. https://tools.thermofisher.com/content/sfs/brochures/1602163-Crosslinking-Reagents-Handbook.pdf.
Thompson (1986) "Structure, function, and molecular defects of factor IX," Blood, vol. 67 No. 3, pp. 565-572.
Thurman et al. (1988) "Characterization of the effect of aluminum metal on poliovirus," Journal of Industrial Microbiology, 3, pp. 33-38.
UnitProt Consortium. (2017a). UniProtKB—P00734 (thrb_human). Retrieved Feb. 4, 2017, from http://www.uniprot.org/uniprot/P00734.
UnitProt Consortium. (2017b). UniProtKB—P00740 (fa9_human). Retrieved Apr. 4, 2017, from http://www.uniprot.org/uniprot/P00740.
UnitProt Consortium. (2017c). UniProtKB—P07225 (pros_human). Retrieved Mar. 18, 2017, from http://www.uniprot.org/uniprot/P07225.
Van Overmeere et al. (2010) "What controls the pore spacing in porous anodic oxides?," Electrochemistry Communications, vol. 12, pp. 1174-1176.
Vashist et al. (2011) "Effect of antibody immobilization strategies on the analytical performance of a surface plasmon resonance-based immunoassay," Analyst, vol. 136, pp. 4431-4436.
Walker (1981) "Regulation of activated protein C by protein S. The role of phospholipid in factor va inactivation," The Journal of Biological Chemistry, 256(21), pp. 11128-11131.
Walz et al. (1977) "Amino acid sequence of human prothrombin fragments 1 and 2," Proceedings of the National Academy of Sciences of the United States of America, 74(5), pp. 1969-1972.
Wefers et al. (1987) "Oxides and Hydroxides of Aluminum: Alcoa Technical Paper No. 19, Revised," Alcoa Laboratories, 100 pp.
Yim et al. (2007) "Parameter effects for the growth of thin porous anodic aluminum oxides," ECS Transactions, vol. 6, No. 8, pp. 267-274.
Zhu et al. (2011) "Size-tunable porous anodic alumina nanostructure for biosensing," Soft Nanoscience Letters, vol. 1, No. 3, pp. 55-60.
Office Action mailed Apr. 4, 2023 in corresponding Japanese Patent Application No. P2020-566866.
First Examination Report mailed Jul. 6, 2022 in corresponding India Patent Application No. 202047040109.
Office Action mailed Jan. 9, 2024 in corresponding Japanese Patent Application No. 2020-566866.
Office Action mailed Nov. 22, 2023 in corresponding Korean Patent Application No. 10-2020-7027182.
Office Action mailed Dec. 19, 2023 in corresponding Canadian Patent Application No. CA2019050204.

SEQUENCE LISTING

```
<160> NUMBER OF SEQ ID NOS: 21

<210> SEQ ID NO 1
<211> LENGTH: 579
<212> TYPE: PRT
<213> ORGANISM: Homo Sapiens
<220> FEATURE:
<221> NAME/KEY: MISC_FEATURE
<222> LOCATION: (1)..(35)
<223> OTHER INFORMATION: Gla domain of Prothrombin
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
```

<221> NAME/KEY: MISC_FEATURE
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue
<220> FEATURE:
<221> NAME/KEY: MISC_FEATURE
<222> LOCATION: (32)..(32)
<223> OTHER INFORMATION: Xaa is a gamma-carboxyglutamic acid residue

<400> SEQUENCE: 1

```
Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350
```

```
Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
            405                 410                 415

Asp Arg Asp Ile Ala Leu Met Lys Leu Lys Pro Val Ala Phe Ser
                420                 425                 430

Asp Tyr Ile His Pro Val Cys Leu Pro Asp Arg Glu Thr Ala Ala Ser
            435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
            485                 490                 495

Thr Arg Ile Arg Ile Thr Asp Asn Met Phe Cys Ala Gly Tyr Lys Pro
                500                 505                 510

Asp Glu Gly Lys Arg Gly Asp Ala Cys Glu Gly Asp Ser Gly Gly Pro
            515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
            565                 570                 575

Phe Gly Glu

<210> SEQ ID NO 2
<211> LENGTH: 415
<212> TYPE: PRT
<213> ORGANISM: Homo Sapiens
<220> FEATURE:
<221> NAME/KEY: MISC_FEATURE
<222> LOCATION: (1)..(415)
<223> OTHER INFORMATION: Factor IX

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
```

```
                    115                 120                 125
Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                    165                 170                 175

Asp Phe Thr Arg Val Val Gly Gly Asp Ala Lys Pro Gly Gln Phe
                180                 185                 190

Pro Trp Gln Val Val Leu Asn Gly Lys Val Asp Ala Phe Cys Gly Gly
            195                 200                 205

Ser Ile Val Asn Glu Lys Trp Ile Val Thr Ala Ala His Cys Val Glu
        210                 215                 220

Thr Gly Val Lys Ile Thr Val Val Ala Gly His Asn Ile Glu Glu
225                 230                 235                 240

Thr Glu His Thr Glu Gln Lys Arg Asn Val Ile Arg Ile Ile Pro His
                    245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
            275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                    325                 330                 335

Leu Arg Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
            355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                    405                 410                 415

<210> SEQ ID NO 3
<211> LENGTH: 635
<212> TYPE: PRT
<213> ORGANISM: Homo Sapiens
<220> FEATURE:
<221> NAME/KEY: MISC_FEATURE
<222> LOCATION: (1)..(635)
<223> OTHER INFORMATION: Protein S

<400> SEQUENCE: 3

Ala Asn Ser Leu Leu Glu Glu Thr Lys Gln Gly Asn Leu Glu Arg Glu
1               5                   10                  15

Cys Ile Glu Glu Leu Cys Asn Lys Glu Glu Ala Arg Glu Val Phe Glu
                20                  25                  30

Asn Asp Pro Glu Thr Asp Tyr Phe Tyr Pro Lys Tyr Leu Val Cys Leu
            35                  40                  45

Arg Ser Phe Gln Thr Gly Leu Phe Thr Ala Ala Arg Gln Ser Thr Asn
        50                  55                  60
```

```
Ala Tyr Pro Asp Leu Arg Ser Cys Val Asn Ala Ile Pro Asp Gln Cys
 65                  70                  75                  80

Ser Pro Leu Pro Cys Asn Glu Asp Gly Tyr Met Ser Cys Lys Asp Gly
             85                  90                  95

Lys Ala Ser Phe Thr Cys Thr Cys Lys Pro Gly Trp Gln Gly Glu Lys
            100                 105                 110

Cys Glu Phe Asp Ile Asn Glu Cys Lys Asp Pro Ser Asn Ile Asn Gly
        115                 120                 125

Gly Cys Ser Gln Ile Cys Asp Asn Thr Pro Gly Ser Tyr His Cys Ser
    130                 135                 140

Cys Lys Asn Gly Phe Val Met Leu Ser Asn Lys Lys Asp Cys Lys Asp
145                 150                 155                 160

Val Asp Glu Cys Ser Leu Lys Pro Ser Ile Cys Gly Thr Ala Val Cys
                165                 170                 175

Lys Asn Ile Pro Gly Asp Phe Glu Cys Glu Cys Pro Glu Gly Tyr Arg
            180                 185                 190

Tyr Asn Leu Lys Ser Lys Ser Cys Glu Asp Ile Asp Glu Cys Ser Glu
        195                 200                 205

Asn Met Cys Ala Gln Leu Cys Val Asn Tyr Pro Gly Gly Tyr Thr Cys
    210                 215                 220

Tyr Cys Asp Gly Lys Lys Gly Phe Lys Leu Ala Gln Asp Gln Lys Ser
225                 230                 235                 240

Cys Glu Val Val Ser Val Cys Leu Pro Leu Asn Leu Asp Thr Lys Tyr
                245                 250                 255

Glu Leu Leu Tyr Leu Ala Glu Gln Phe Ala Gly Val Val Leu Tyr Leu
            260                 265                 270

Lys Phe Arg Leu Pro Glu Ile Ser Arg Phe Ser Ala Glu Phe Asp Phe
        275                 280                 285

Arg Thr Tyr Asp Ser Glu Gly Val Ile Leu Tyr Ala Glu Ser Ile Asp
    290                 295                 300

His Ser Ala Trp Leu Leu Ile Ala Leu Arg Gly Gly Lys Ile Glu Val
305                 310                 315                 320

Gln Leu Lys Asn Glu His Thr Ser Lys Ile Thr Thr Gly Gly Asp Val
                325                 330                 335

Ile Asn Asn Gly Leu Trp Asn Met Val Ser Val Glu Glu Leu Glu His
            340                 345                 350

Ser Ile Ser Ile Lys Ile Ala Lys Glu Ala Val Met Asp Ile Asn Lys
        355                 360                 365

Pro Gly Pro Leu Phe Lys Pro Glu Asn Gly Leu Leu Glu Thr Lys Val
    370                 375                 380

Tyr Phe Ala Gly Phe Pro Arg Lys Val Glu Ser Glu Leu Ile Lys Pro
385                 390                 395                 400

Ile Asn Pro Arg Leu Asp Gly Cys Ile Arg Ser Trp Asn Leu Met Lys
                405                 410                 415

Gln Gly Ala Ser Gly Ile Lys Glu Ile Gln Glu Lys Gln Asn Lys
            420                 425                 430

His Cys Leu Val Thr Val Glu Lys Gly Ser Tyr Tyr Pro Gly Ser Gly
        435                 440                 445

Ile Ala Gln Phe His Ile Asp Tyr Asn Asn Val Ser Ser Ala Glu Gly
    450                 455                 460

Trp His Val Asn Val Thr Leu Asn Ile Arg Pro Ser Thr Gly Thr Gly
465                 470                 475                 480
```

-continued

```
Val Met Leu Ala Leu Val Ser Gly Asn Asn Thr Val Pro Phe Ala Val
                485                 490                 495

Ser Leu Val Asp Ser Thr Ser Glu Lys Ser Gln Asp Ile Leu Leu Ser
            500                 505                 510

Val Glu Asn Thr Val Ile Tyr Arg Ile Gln Ala Leu Ser Leu Cys Ser
        515                 520                 525

Asp Gln Gln Ser His Leu Glu Phe Arg Val Asn Arg Asn Asn Leu Glu
    530                 535                 540

Leu Ser Thr Pro Leu Lys Ile Glu Thr Ile Ser His Glu Asp Leu Gln
545                 550                 555                 560

Arg Gln Leu Ala Val Leu Asp Lys Ala Met Lys Ala Lys Val Ala Thr
                565                 570                 575

Tyr Leu Gly Gly Leu Pro Asp Val Pro Phe Ser Ala Thr Pro Val Asn
            580                 585                 590

Ala Phe Tyr Asn Gly Cys Met Glu Val Asn Ile Asn Gly Val Gln Leu
        595                 600                 605

Asp Leu Asp Glu Ala Ile Ser Lys His Asn Asp Ile Arg Ala His Ser
    610                 615                 620

Cys Pro Ser Val Trp Lys Lys Thr Lys Asn Ser
625                 630                 635

<210> SEQ ID NO 4
<211> LENGTH: 151
<212> TYPE: PRT
<213> ORGANISM: Artificial
<220> FEATURE:
<223> OTHER INFORMATION: Engineered
<220> FEATURE:
<221> NAME/KEY: MISC_FEATURE
<222> LOCATION: (1)..(35)
<223> OTHER INFORMATION: Engineered Gla domain of F1 Asp

<400> SEQUENCE: 4

Ala Asn Thr Phe Leu Asp Asp Val Arg Lys Gly Asn Leu Asp Arg Asp
1               5                   10                  15

Cys Val Asp Asp Thr Cys Ser Tyr Asp Asp Ala Phe Asp Ala Leu Asp
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Met Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala
145                 150

<210> SEQ ID NO 5
<211> LENGTH: 161
<212> TYPE: PRT
<213> ORGANISM: Artificial
```

```
<220> FEATURE:
<223> OTHER INFORMATION: Engineered
<220> FEATURE:
<221> NAME/KEY: MISC_FEATURE
<222> LOCATION: (1)..(45)
<223> OTHER INFORMATION: Engineered Gla domain of F1 AspAsp

<400> SEQUENCE: 5

Ala Asn Thr Phe Leu Asp Asp Asp Val Arg Lys Gly Asn Leu Asp
1               5                   10                  15

Asp Arg Asp Asp Cys Val Asp Asp Asp Thr Cys Ser Tyr Asp Asp
            20                  25                  30

Asp Asp Ala Phe Asp

Ser Ser Thr Met Gly Pro Trp Cys Tyr Thr Thr Asp Pro Thr Val Arg
    130                 135                 140

Arg Gln Glu Cys Ser Ile Pro Val Cys Gly Gln Asp Gln Val Thr Val
145                 150                 155                 160

Ala

<210> SEQ ID NO 7
<211> LENGTH: 161
<212> TYPE: PRT
<213> ORGANISM: Artificial
<220> FEATURE:
<223> OTHER INFORMATION: Engineered
<220> FEATURE:
<221> NAME/KEY: MISC_FEATURE
<222> LOCATION: (1)..(45)
<223> OTHER INFORMATION: Engineered Gla domain of F1 GluAsp

<400> SEQUENCE: 7

Ala Asn Thr Phe Leu Glu Asp Glu Val Arg Lys Gly Asn Leu Glu
1               5                   10

-continued

```
Asp Lys Leu Ala Ala Cys Leu Glu Gly Asn Cys Ala Glu Gly Leu Gly
 65                  70                  75                  80

Thr Asn Tyr Arg Gly His Val Asn Ile Thr Arg Ser Gly Ile Glu Cys
                 85                  90                  95

Gln Leu Trp Arg Ser Arg Tyr Pro His Lys Pro Glu Ile Asn Ser Thr
            100                 105                 110

Thr His Pro Gly Ala Asp Leu Gln Glu Asn Phe Cys Arg Asn Pro Asp
        115                 120                 125

Ser Ser Thr Met Gly Pro Trp Cys Tyr Thr Thr Asp Pro Thr Val Arg
130                 135                 140

Arg Gln Glu Cys Ser Ile Pro Val Cys Gly Gln Asp Gln Val Thr Val
145                 150                 155                 160

Ala

<210> SEQ ID NO 9
<211> LENGTH: 156
<212> TYPE: PRT
<213> ORGANISM: Bos taurus
<220> FEATURE:
<221> NAME/KEY: MISC_FEATURE
<222> LOCATION: (1)..(33)
<223> OTHER INFORMATION: Gla domain of F1 bos taurus factor II
<220> FEATURE:
<221> NAME/KEY: MISC_FEATURE
<222> LOCATION: (7)..(8)
<223> OTHER INFORMATION: Xaa is a gamma-carboxyglutamic acid residue
<220> FEATURE:
<221> NAME/KEY: MISC_FEATURE
<222> LOCATION: (15)..(15)
<223> OTHER INFORMATION: Xaa is a gamma-carboxyglutamic acid residue
<220> FEATURE:
<221> NAME/KEY: MISC_FEATURE
<222> LOCATION: (17)..(17)
<223> OTHER INFORMATION: Xaa is a gamma-carboxyglutamic acid residue
<220> FEATURE:
<221> NAME/KEY: MISC_FEATURE
<222> LOCATION: (20)..(21)
<223> OTHER INFORMATION: Xaa is a gamma-carboxyglutamic acid residue
<220> FEATURE:
<221> NAME/KEY: MISC_FEATURE
<222> LOCATION: (26)..(27)
<223> OTHER INFORMATION: Xaa is a gamma-carboxyglutamic acid residue
<220> FEATURE:
<221> NAME/KEY: MISC_FEATURE
<222> LOCATION: (30)..(30)
<223> OTHER INFORMATION: Xaa is a gamma-carboxyglutamic acid residue
<220> FEATURE:
<221> NAME/KEY: MISC_FEATURE
<222> LOCATION: (33)..(33)
<223> OTHER INFORMATION: Xaa is a gamma-carboxyglutamic acid residue

<400> SEQUENCE: 9

Ala Asn Lys Gly Phe Leu Xaa Xaa Val Arg Lys Gly Asn Leu Xaa Arg
 1               5                  10                  15

Xaa Cys Leu Xaa Xaa Pro Cys Ser Arg Xaa Xaa Ala Phe Xaa Ala Leu
                 20                  25                  30

Xaa Ser Leu Ser Ala Thr Asp Ala Phe Trp Ala Lys Tyr Thr Ala Cys
             35                  40                  45

Glu Ser Ala Arg Asn Pro Arg Glu Lys Leu Asn Glu Cys Leu Glu Gly
         50                  55                  60

Asn Cys Ala Glu Gly Val Gly Met Asn Tyr Arg Gly Asn Val Ser Val
 65                  70                  75                  80

Thr Arg Ser Gly Ile Glu Cys Gln Leu Trp Arg Ser Arg Tyr Pro His
                 85                  90                  95
```

```
Lys Pro Glu Ile Asn Ser Thr Thr His Pro Gly Ala Asp Leu Arg Glu
            100                 105                 110

Asn Phe Cys Arg Asn Pro Asp Gly Ser Ile Thr Gly Pro Trp Cys Tyr
            115                 120                 125

Thr Thr Ser Pro Thr Leu Arg Arg Glu Glu Cys Ser Val Pro Val Cys
            130                 135                 140

Gly Gln Asp Arg Val Thr Val Glu Val Ile Pro Arg
145                 150                 155

<210> SEQ ID NO 10
<211> LENGTH: 365
<212> TYPE: PRT
<213> ORGANISM: Artificial
<220> FEATURE:
<223> OTHER INFORMATION: Engineered
<220> FEATURE:
<221> NAME/KEY: MISC_FEATURE
<222> LOCATION: (331)..(365)
<223> OTHER INFORMATION: Engineered IgG with added F1 modified with Asp
      replacing Gla at the carboxyl terminal of IgG

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
            275                 280                 285
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Ala Asn Thr Phe Leu Asp
            325                 330                 335

Asp Val Arg Lys Gly Asn Leu Asp Arg Asp Cys Val Asp Asp Thr Cys
            340                 345                 350

Ser Tyr Asp Asp Ala Phe Asp Ala Leu Asp Ser Ser Thr
            355                 360                 365

<210> SEQ ID NO 11
<211> LENGTH: 365
<212> TYPE: PRT
<213> ORGANISM: Artificial
<220> FEATURE:
<223> OTHER INFORMATION: Engineered
<220> FEATURE:
<221> NAME/KEY: MISC_FEATURE
<222> LOCATION: (331)..(365)
<223> OTHER INFORMATION: Engineered IgG with added F1 modified with Glu
      replacing Gla at the carboxyl terminal of IgG

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Ala Asn Thr Phe Leu Glu
                325                 330                 335

Glu Val Arg Lys Gly Asn Leu Glu Arg Glu Cys Val Glu Glu Thr Cys
            340                 345                 350

Ser Tyr Glu Glu Ala Phe Glu Ala Leu Glu Ser Ser Thr
        355                 360                 365

<210> SEQ ID NO 12
<211> LENGTH: 93
<212> TYPE: PRT
<213> ORGANISM: Artificial
<220> FEATURE:
<223> OTHER INFORMATION: Frag B of protein A with 35 amino acids of F1
<220> FEATURE:
<221> NAME/KEY: MISC_FEATURE
<222> LOCATION: (64)..(65)
<223> OTHER INFORMATION: Xaa is a gamma-carboxyglutamic acid residue
<220> FEATURE:
<221> NAME/KEY: MISC_FEATURE
<222> LOCATION: (72)..(72)
<223> OTHER INFORMATION: Xaa is a gamma-carboxyglutamic acid residue
<220> FEATURE:
<221> NAME/KEY: MISC_FEATURE
<222> LOCATION: (74)..(74)
<223> OTHER INFORMATION: Xaa is a gamma-carboxyglutamic acid residue
<220> FEATURE:
<221> NAME/KEY: MISC_FEATURE
<222> LOCATION: (77)..(78)
<223> OTHER INFORMATION: Xaa is a gamma-carboxyglutamic acid residue
<220> FEATURE:
<221> NAME/KEY: MISC_FEATURE
<222> LOCATION: (83)..(84)
<223> OTHER INFORMATION: Xaa is a gamma-carboxyglutamic acid residue
<220> FEATURE:
<221> NAME/KEY: MISC_FEATURE
<222> LOCATION: (87)..(87)
<223> OTHER INFORMATION: Xaa is a gamma-carboxyglutamic acid residue
<220> FEATURE:
<221> NAME/KEY: MISC_FEATURE
<222> LOCATION: (90)..(90)
<223> OTHER INFORMATION: Xaa is a gamma-carboxyglutamic acid residue

<400> SEQUENCE: 12

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala Asn Thr Phe Leu Xaa
    50                  55                  60

Xaa Val Arg Lys Gly Asn Leu Xaa Arg Xaa Cys Val Xaa Xaa Thr Cys
65                  70                  75                  80

Ser Tyr Xaa Xaa Ala Phe Xaa Ala Leu Xaa Ser Ser Thr
                85                  90
```

```
<210> SEQ ID NO 13
<211> LENGTH: 45
<212> TYPE: PRT
<213> ORGANISM: Artificial
<220> FEATURE:
<223> OTHER INFORMATION: Factor X Gla
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
<221> NAME/KEY: MISC_FEATURE
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue
<220> FEATURE:
<221> NAME/KEY: MISC_FEATURE
<222> LOCATION: (32)..(32)
<223> OTHER INFORMATION: Xaa is a gamma-carboxyglutamic acid residue
<220> FEATURE:
<221> NAME/KEY: MISC_FEATURE
<222> LOCATION: (39)..(39)
<223> OTHER INFORMATION: Xaa is a gamma-carboxyglutamic acid residue

<400> SEQUENCE: 13

Ala Asn Ser Phe Leu Xaa Xaa Met Lys Lys Gly His Leu Xaa Arg Xaa
1               5                   10                  15

Cys Met Xaa Xaa Thr Cys Ser Tyr Xaa Xaa Ala Arg Xaa Val Phe Xaa
            20                  25                  30

Asp Ser Asp Lys Thr Asn Xaa Phe Trp Asn Lys Tyr Lys
        35                  40                  45

<210> SEQ ID NO 14
<211> LENGTH: 35
<212> TYPE: PRT
<213> ORGANISM: Artificial
<220> FEATURE:
<223> OTHER INFORMATION: Factor II Gla
<220> FEATURE:
<221> NAME/KEY: MISC_FEATURE
<222> LOCATION: (1)..(35)
<223> OTHER INFORMATION: Gla domain of prothrombin
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
<221> NAME/KEY: MISC_FEATURE
```

```
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue
<220> FEATURE:
<221> NAME/KEY: MISC_FEATURE
<222> LOCATION: (32)..(32)
<223> OTHER INFORMATION: Xaa is a gamma-carboxyglutamic acid residue

<400> SEQUENCE: 14

Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
            20                  25                  30

Ser Ser Thr
        35

<210> SEQ ID NO 15
<211> LENGTH: 46
<212> TYPE: PRT
<213> ORGANISM: Homo Sapiens
<220> FEATURE:
<221> NAME/KEY: MISC_FEATURE
<223> OTHER INFORMATION: Protein C Gla
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
<221> NAME/KEY: MISC_FEATURE
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue

<400> SEQUENCE: 15

Ala Asn Ser Phe Leu Xaa Xaa Leu Arg His Ser Ser Leu Xaa Arg Xaa
1               5                   10                  15

Cys Ile Xaa Xaa Ile Cys Asp Phe Xaa Xaa Ala Lys Xaa Ile Phe Gln
            20                  25                  30

Asn Val Asp Asp Thr Leu Ala Phe Trp Ser Lys His Val Asp
            35                  40                  45

<210> SEQ ID NO 16
<211> LENGTH: 45
<212> TYPE: PRT
<213> ORGANISM: Homo Sapiens
<220> FEATURE:
<221> NAME/KEY: MISC_FEATURE
<223> OTHER INFORMATION: Factor VII Gla
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
```

<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
<221> NAME/KEY: MISC_FEATURE
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue
<220> FEATURE:
<221> NAME/KEY: MISC_FEATURE
<222> LOCATION: (35)..(35)
<223> OTHER INFORMATION: Xaa is a gamma-carboxyglutamic acid residue

<400> SEQUENCE: 16

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser
        35                  40                  45

<210> SEQ ID NO 17
<211> LENGTH: 46
<212> TYPE: PRT
<213> ORGANISM: Homo Sapiens
<220> FEATURE:
<221> NAME/KEY: MISC_FEATURE
<223> OTHER INFORMATION: Protein Z Gla
<220> FEATURE:
<221> NAME/KEY: MISC_FEATURE
<222> LOCATION: (7)..(8)
<223> OTHER INFORMATION: Xaa is a gamma-carboxyglutamic acid residue
<220> FEATURE:
<221> NAME/KEY: MISC_FEATURE
<222> LOCATION: (11)..(11)
<223> OTHER INFORMATION: Xaa is a gamma-carboxyglutamic acid residue
<220> FEATURE:
<221> NAME/KEY: MISC_FEATURE
<222> LOCATION: (15)..(15)
<223> OTHER INFORMATION: Xaa is a gamma-carboxyglutamic acid residue
<220> FEATURE:
<221> NAME/KEY: MISC_FEATURE
<222> LOCATION: (17)..(17)
<223> OTHER INFORMATION: Xaa is a gamma-carboxyglutamic acid residue
<220> FEATURE:
<221> NAME/KEY: MISC_FEATURE
<222> LOCATION: (20)..(21)
<223> OTHER INFORMATION: Xaa is a gamma-carboxyglutamic acid residue
<220> FEATURE:
<221> NAME/KEY: MISC_FEATURE
<222> LOCATION: (26)..(27)
<223> OTHER INFORMATION: Xaa is a gamma-carboxyglutamic acid residue
<220> FEATURE:
<221> NAME/KEY: MISC_FEATURE
<222> LOCATION: (30)..(30)
<223> OTHER INFORMATION: Xaa is a gamma-carboxyglutamic acid residue
<220> FEATURE:
<221> NAME/KEY: MISC_FEATURE
<222> LOCATION: (33)..(33)
<223> OTHER INFORMATION: Xaa is a gamma-carboxyglutamic acid residue
<220> FEATURE:
<221> NAME/KEY: MISC_FEATURE
<222> LOCATION: (35)..(35)
<223> OTHER INFORMATION: Xaa is a gamma-carboxyglutamic acid residue

```
<220> FEATURE:
<221> NAME/KEY: MISC_FEATURE
<222> LOCATION: (40)..(40)
<223> OTHER INFORMATION: Xaa is a gamma-carboxyglutamic acid residue

<400> SEQUENCE: 17

Ala Gly Ser Tyr Leu Leu Xaa Xaa Leu Phe Xaa Gly Asn Leu Xaa Lys
1               5                   10                  15

Xaa Cys Tyr Xaa Xaa Ile Cys Val Tyr Xaa Xaa Ala Arg Xaa Val Phe
                20                  25                  30

Xaa Asn Xaa Val Val Thr Asp Xaa Phe Trp Arg Arg Tyr Lys
            35                  40                  45

<210> SEQ ID NO 18
<211> LENGTH: 45
<212> TYPE: PRT
<213> ORGANISM: Artificial
<220> FEATURE:
<223> OTHER INFORMATION: Engineered Peptide with Gla
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
<221> NAME/KEY: MISC_FEATURE
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue
<220> FEATURE:
<221> NAME/KEY: MISC_FEATURE
<222> LOCATION: (32)..(32)
<223> OTHER INFORMATION: Xaa is a gamma-carboxyglutamic acid residue
<220> FEATURE:
<221> NAME/KEY: MISC_FEATURE
<222> LOCATION: (36)..(36)
<223> OTHER INFORMATION: Xaa is a gamma-carboxyglutamic acid residue

<400> SEQUENCE: 18

Ala Asn Ser Leu Leu Xaa Xaa Thr Lys Gln Gly Asn Leu Xaa Arg Xaa
1               5                   10                  15

Cys Ile Xaa Xaa Leu Cys Asn Lys Xaa Xaa Ala Arg Xaa Val Phe Xaa
                20                  25                  30

Asn Asp Pro Xaa Thr Asp Tyr Phe Tyr Pro Lys Tyr Leu
            35                  40                  45

<210> SEQ ID NO 19
<211> LENGTH: 143
<212> TYPE: PRT
<213> ORGANISM: Artificial
<220> FEATURE:
<223> OTHER INFORMATION: Factor II Gla with Kringle
<220> FEATURE:
<221> NAME/KEY: MISC_FEATURE
<222> LOCATION: (6)..(7)
<223> OTHER INFORMATION: Xaa is a gamma-carboxyglutamic acid residue
<220> FEATURE:
```

```
<221> NAME/KEY: MISC_FEATURE
<222> LOCATION: (14)..(14)
<223> OTHER INFORMATION: Xaa is a gamma-carboxyglutamic acid residue
<220> FEATURE:
<221> NAME/KEY: MISC_FEATURE
<222> LOCATION: (16)..(16)
<223> OTHER INFORMATION: Xaa is a gamma-carboxyglutamic acid residue
<220> FEATURE:
<221> NAME/KEY: MISC_FEATURE
<222> LOCATION: (19)..(20)
<223> OTHER INFORMATION: Xaa is a gamma-carboxyglutamic acid residue
<220> FEATURE:
<221> NAME/KEY: MISC_FEATURE
<222> LOCATION: (25)..(26)
<223> OTHER INFORMATION: Xaa is a gamma-carboxyglutamic acid residue
<220> FEATURE:
<221> NAME/KEY: MISC_FEATURE
<222> LOCATION: (29)..(29)
<223> OTHER INFORMATION: Xaa is a gamma-carboxyglutamic acid residue
<220> FEATURE:
<221> NAME/KEY: MISC_FEATURE
<222> LOCATION: (32)..(32)
<223> OTHER INFORMATION: Xaa is a gamma-carboxyglutamic acid residue
<220> FEATURE:
<221> NAME/KEY: MISC_FEATURE
<222> LOCATION: (48)..(48)
<223> OTHER INFORMATION: Xaa is a gamma-carboxyglutamic acid residue
<220> FEATURE:
<221> NAME/KEY: MISC_FEATURE
<222> LOCATION: (62)..(62)
<223> OTHER INFORMATION: Xaa is a gamma-carboxyglutamic acid residue
<220> FEATURE:
<221> NAME/KEY: MISC_FEATURE
<222> LOCATION: (67)..(67)
<223> OTHER INFORMATION: Xaa is a gamma-carboxyglutamic acid residue
<220> FEATURE:
<221> NAME/KEY: MISC_FEATURE
<222> LOCATION: (85)..(85)
<223> OTHER INFORMATION: Xaa is a gamma-carboxyglutamic acid residue
<220> FEATURE:
<221> NAME/KEY: MISC_FEATURE
<222> LOCATION: (98)..(98)
<223> OTHER INFORMATION: Xaa is a gamma-carboxyglutamic acid residue
<220> FEATURE:
<221> NAME/KEY: MISC_FEATURE
<222> LOCATION: (111)..(111)
<223> OTHER INFORMATION: Xaa is a gamma-carboxyglutamic acid residue
<220> FEATURE:
<221> NAME/KEY: MISC_FEATURE
<222> LOCATION: (137)..(137)
<223> OTHER INFORMATION: Xaa is a gamma-carboxyglutamic acid residue

<400> SEQUENCE: 19

Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
                20                  25                  30

Ser Ser Thr Ala Thr Asp Val Phe Trp Ala Lys Tyr Thr Ala Cys Xaa
            35                  40                  45

Thr Ala Arg Thr Pro Arg Asp Lys Leu Ala Ala Cys Leu Xaa Gly Asn
        50                  55                  60

Cys Ala Xaa Gly Leu Gly Thr Asn Tyr Arg Gly His Val Asn Ile Thr
65                  70                  75                  80

Arg Ser Gly Ile Xaa Cys Gln Leu Trp Arg Ser Arg Tyr Pro His Lys
                85                  90                  95

Pro Xaa Ile Asn Ser Thr Thr His Pro Gly Ala Asp Leu Gln Xaa Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Xaa Cys Ser Ile Pro Val Cys
```

-continued

```
                130                 135                 140

<210> SEQ ID NO 20
<211> LENGTH: 5
<212> TYPE: PRT
<213> ORGANISM: Artificial
<220> FEATURE:
<223> OTHER INFORMATION: Fusion Linker

<400> SEQUENCE: 20

Gly Gly Gly Gly Ser
1               5

<210> SEQ ID NO 21
<211> LENGTH: 11
<212> TYPE: PRT
<213> ORGANISM: Artificial
<220> FEATURE:
<223> OTHER INFORMATION: Open Reading Frame

<400> SEQUENCE: 21

Thr Gln Lys Ser Leu Ser Leu Ser Pro Gly Lys
1               5                   10
```

US 12,061,195 B2

ALUMINUM OXIDE SURFACES AND INTERFACE MOLECULES

CROSS-REFERENCE TO RELATED APPLICATIONS

This application is a U.S. National Stage Application filed under 35 U.S.C. § 371 of International Application No. PCT/CA2019/050204, filed Feb. 20, 2019, which claims the benefit of U.S. Provisional Application No. 62/633,009, filed Feb. 20, 2018. Both of these applications are hereby incorporated by reference in their entireties.

FIELD OF THE INVENTION

This invention relates to aluminum oxide surfaces for attaching biomolecules such as proteins for use in biomedical or industrial applications. The aluminum oxide surfaces are useful for applications such as diagnostic testing, affinity assays, and isolating biomolecules of interest from complex mixtures of biomolecules.

BACKGROUND

Over the last 50 years the need for immobilized biomolecules has grown significantly. Early efforts to immobilize biomolecules were for diagnostics such as ELISA assays. In these assays antibodies were added to polymer surfaces such as microtiter dishes. These surfaces were often polystyrene. The immobilized antibodies were only 5 to 7% active as the antibodies were randomly adsorbed to the surface. It was recognized that sensitivity of ELISA assays could be increased by an order magnitude if the antibodies were oriented on the surface such that the Fab fragments were directed away from the surface and the actual binding to the surface occurred through the Fc fragment. The need for oriented immobilized biomolecules has increased with time. Microfluidic devices, gene and protein microarrays and immunodiagnostics in general all benefit from oriented binding. Further analytical techniques such as quartz microbalances, surface plasmon resonance and capillary electrophoresis all benefit from improved oriented binding. Industrial processes such as affinity chromatography and affinity separations have improved efficiency if all the proteins were ordered on the surface properly. Equally important in all of these fields is the need to prevent nonspecific protein binding.

Protein adsorption on oxides is very important in the area of bioceramics. Titania, alumina, and zirconia are some of the more common oxide ceramics used for medical applications. Due to their excellent material properties, such as corrosion resistance, wear resistance, biocompatibility and mechanical strength, these materials are often used in medicine and dentistry as biomaterials. Protein adsorption to oxides must take into account many material and environmental aspects, such as pH, microstructure, zeta-potential, and surface reactivity.

Proteins and other biomolecules such as DNA and RNA readily adsorb onto surfaces, particularly if they are charged. Attempts to improve the adsorption process have included activating the surface chemically or physically to increase the number of charged sites. When materials such as alumina are considered, which are highly catalytic, the proteins adsorbed may be denatured. There is ample evidence in the literature to show that this is a common phenomena (Murray and Laband, 1979; Murray, 1980; Thurman and Gerba, 1988; Bowen and Gan, 1992). Since the adsorption process tends to be random it can also lead to inappropriate binding which may lead to steric hindrance. If molecules are oriented inappropriately or if they pack too tightly, steric hindrance occurs. If the desired proteins do not cover the surface fully nonspecific binding can become a significant problem.

Polymer networks, such as hydrogels, will hold water in which other molecules can be dissolved. These molecules are then available for reactions. The drawbacks to these techniques include the thickness of the thin-film and diffusion processes which may generate slow responses. Others have attempted to use thin polymer films to coat surfaces such as alumina. The polymers have exposed pendant groups which are then used to covalently bond to the biomolecules. This technique helps solve the problem of the overly thick thin-film but can lead to nonspecific binding and poor orientation.

On glass and silica surfaces the most common technique for covalently bonding biomolecules to the surface is through a silanation process. In these processes triethoxysilane derivatives are added to the surface where the ethoxygroups react with the silicon hydroxide groups on the surface with the release of ethanol to form a silated surface. The silicon in the tri-ethoxysilane derivative is linked to a group that determines the surface properties. If this group is a long chain alkane the surface becomes hydrophobic, whereas if the group is a methyl group the surface becomes hydrophilic. These groups are then used to link covalently to biomolecules. In these cases the biomolecules may be an antibody, an antigen, DNA, RNA, or a molecule like avidin. Mao et al. (U.S. Pat. No. 8,178,602) have shown such a system using R-PEG-silane as a preferred way to functionalize a surface. The R group in their example is either biotin or methoxy. When they use a blend of the two surface modifying molecules the methoxy component is a neutral spacer which reduces steric hindrance and allows the biotin to bind more avidin. Wagner et al. (U.S. Pat. No. 6,596,545) show that a silane can be used to bind a linker molecule to glass or a thiol can be used to bind a sulphur-containing linker molecule to a gold surface. These linkers can then be attached to a biomolecule of interest. Coyne et al. (U.S. Pat. No. 6,589,799) demonstrated activating surface hydroxyl groups on a support matrix material and reacting the activated hydroxyl groups with an aldehydic alkoxy silane. The derivatized aldehydic support matrix material was then useful for immobilizing biomolecules and biological applications.

Other covalent techniques include the use of calixarene. If the metal oxide surface is first reacted with $SiCl_4$ to create a silicon chloride surface then that silicon chloride can be reacted with the calixarene to form a stable structure on the surface. This structure can have biomolecules covalently attached to it. (Katz et al. U.S. Pat. No. 6,951,690)

SUMMARY

The inventor discovered that an aluminum oxide surface can be reliably refunctionalized for biomedical applications with an interface molecule having a carboxy rich domain. In particular, the interface molecule includes a polypeptide having at least one carboxy rich domain providing at least 5 free carboxyl groups within a molecular volume of 2.2-25 $nm^3$, the free carboxyl groups being provided by amino acids containing two or more carboxyl groups, through with the interface molecule is immobilized to the aluminum oxide surface. The interface molecule is immobilized on the aluminum oxide surface, and a biomolecule or a cross linking agent is attached to the interface molecule. This aluminum oxide/interface molecule structure or device provides a base, for example, for a diagnostic device or an affinity assay, and in a manner that the biomolecule retains its biological identity, and remains attached to the interface molecule in a stable manner.

In one broad aspect, the invention provides a device for use in binding to an analyte of interest. The device includes an aluminum oxide surface and an interface molecule immobilized on the aluminum oxide surface. The interface molecule includes a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is immobilized to the aluminum oxide surface. One of the following is attached to the interface molecule:

i) a cross linking agent for binding to the analyte;

ii) a biomolecule attached to the interface molecule through one or more covalent bonds, the biomolecule being specific to the analyte;

iii) a biomolecule in the form of an engineered antibody attached to the interface molecule through a first antigenic determinant specific to the interface molecule, and having a second antigenic determinant specific to the analyte; and iv) a biomolecule in the form of an engineered antibody attached to the interface molecule though an Fc fragment of the antibody and having Fab fragments specific to the analyte.

The invention also extends to an interface complex for use in binding to an analyte of interest and capable of being immobilized on an aluminum oxide surface. The interface complex includes an interface molecule comprising a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is capable of being immobilized to the aluminum oxide surface. The interface molecule further includes one of:

i) a cross linking agent attached to the interface molecule for binding to an analyte of interest;

ii) a biomolecule attached to the interface molecule through one or more covalent bonds, the biomolecule being specific to an analyte of interest;

iii) a biomolecule in the form of an engineered antibody attached to the interface molecule through a first antigenic determinant specific to the interface molecule, and having a second antigenic determinant specific to an analyte of interest; and iv) a biomolecule in the form of an engineered antibody attached to the interface molecule though an Fc fragment of the antibody and having Fab fragments specific to the analyte of interest.

In another broad aspect, the invention provides a diagnostic system or a kit for testing whether binding has occurred to an analyte of interest. The diagnostic system or kit includes: 1) an aluminum oxide surface and an interface molecule including a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is capable of being immobilized to the aluminum oxide surface, and 2) one of the following:

i) a cross linking agent attached to the interface molecule for binding to the analyte;

ii) a biomolecule attached to the interface molecule through one or more covalent bonds, the biomolecule being specific to the analyte;

iii) a biomolecule in the form of an engineered antibody attached to the interface molecule through a first antigenic determinant specific to the interface molecule, and having a second antigenic determinant specific to the analyte; and iv) a biomolecule in the form of an engineered antibody attached to the interface molecule though an Fc fragment of the antibody and having Fab fragments specific to the analyte.

In some embodiments of the above, the interface molecule and one of (i), (ii), (iii) and (iv) are immobilized on the aluminum oxide surface. In other embodiments the interface molecule and one of (i), (ii), (iii) and (iv) are provided as an interface complex for contact with the analyte prior to immobilizing on the aluminum oxide surface.

Some embodiments of the diagnostic system or kit provide a visual diagnostic device. The aluminum oxide surface is provided on a reflective metal capable of generating a colour when covered by a porous layer of aluminum oxide, and the aluminum oxide surface is a porous anodized surface. In this manner, the visual diagnostic device, when contacted with a sample to test for the analyte, a colour change is detected denoting the presence of the analyte upon binding of the analyte either to the cross linking agent if (i) is present, or to the biomolecule if (ii), (iii) or (iv) is present.

The invention also broadly extends to a method of testing whether binding has occurred to an analyte of interest. The method includes:

a) providing an aluminum oxide surface having an interface molecule immobilized thereon, the interface molecule comprising a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is immobilized to the aluminum oxide surface, the interface molecule being attached to one of:

i) a cross linking agent for binding to the analyte;

ii) a biomolecule specific to an analyte;

iii) a biomolecule in the form of an engineered antibody having a first antigenic determinant specific to the interface molecule, and having a second antigenic determinant specific to the analyte of interest;

iv) a biomolecule in the form of an engineered antibody attached to the interface molecule though an Fc fragment of the antibody and having Fab fragments specific to the analyte of interest;

b) contacting the surface of a) with a sample to test for the analyte; and c) detecting the presence of the analyte upon binding of the analyte to the surface of a).

In some embodiments, the invention broadly extends to a method of testing whether binding has occurred to an analyte of interest. The method includes:

a) providing an aluminum oxide surface;

b) providing an interface complex capable of binding to the aluminum oxide surface, wherein the interface complex includes an interface molecule comprising a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is capable of being immobilized on the aluminum oxide surface, and wherein the interface molecule is attached to one of:

i) a cross linking agent for binding to the analyte;

ii) a biomolecule specific to an analyte;

iii) a biomolecule in the form of an engineered antibody having a first antigenic determinant specific to the interface molecule, and having a second antigenic determinant specific to the analyte of interest; and iv) a biomolecule in the form of an engineered antibody attached to the interface molecule though an Fc fragment of the antibody and having Fab fragments specific to the analyte of interest;

b) contacting the interface complex of a) with a sample to test for the analyte;

c) contacting the sample and the interface complex of b) with the aluminum oxide surface; and d) detecting the presence of the analyte upon binding of the analyte and the interface complex to the aluminum oxide surface.

In some embodiments of the above methods, the aluminum oxide surface is provided on a reflective metal capable of generating a colour when covered by a porous layer of aluminum oxide, and the aluminum oxide surface is a porous anodized surface. In this manner, when contacted with a sample to test for the analyte, a colour change is detected denoting the presence of the analyte upon binding of the analyte either to the cross linking agent if (i) is present, or to the biomolecule if (ii), (iii) or (iv) is present.

In some embodiments of the above device, diagnostic system, kit or method the carboxy rich domain provides:

at least 10 free carboxyl groups within a molecular volume of 2.2-25 $nm^3$; or at least 20 free carboxyl groups within a molecular volume of 2.2-25 $nm^3$; or at least 10 free carboxyl groups within a molecular volume of 2.2-17 $nm^3$, or at least 20 free carboxyl groups within a molecular volume of 2.2-17 $nm^3$; or at least 10 free carboxyl groups within a molecular volume of 7.0-17 $nm^3$, or at least 20 free carboxyl groups within a molecular volume of 7.0-17 $nm^3$.

In some embodiments of the above device, diagnostic system, kit or method:

the cross linking agent is covalently bonded to the interface molecule; or the biomolecule is covalently bonded to the interface molecule through a cross-linking agent; or the interface molecule and the biomolecule are engineered as an amino acid sequence such that the interface molecule and biomolecule are attached through peptide bonds; or the interface molecule is an engineered or synthetic protein, polypeptide or antibody incorporating the carboxy rich domain; or the biomolecule is an engineered antibody having a first antigenic determinant specific to the interface molecule, and having a second antigenic determinant specific to the analyte of interest; or the biomolecule is an engineered antibody attached to the interface molecule though an Fc fragment of the antibody and having Fab fragments specific to the analyte of interest.

In some embodiments, the cross linking agent is covalently bonded to the interface molecule. In other embodiments, the biomolecule is covalently bonded to the interface molecule through a cross-linking agent. In other embodiments, the interface molecule and the biomolecule are engineered as an amino acid sequence such that the interface molecule and biomolecule are attached through peptide bonds. In still further embodiments, the interface molecule is an engineered protein, polypeptide or antibody incorporating the carboxy rich domain.

In some embodiments the interface molecule is provided on the aluminum oxide surface as a continuous or discontinuous coating, as delineated spots or lines, or as an array.

In some embodiments the interface molecule is one of different types of interface molecules spaced on the aluminum oxide surface, with biomolecules attached to one type of the interface molecules.

In some embodiments, the aluminum oxide surface is provided on a substrate in the form of a particle, powder, thin film, slide, strip, bead, magnetic bead, magnetic particle or coating.

In some embodiments, the aluminum oxide surface is provided by sputtering, evaporating, casting or extruding aluminum metal or an aluminum alloy, which is further anodized to provide a porous anodized aluminum oxide surface.

In some embodiments, the aluminum oxide surface is provided by RF sputtering, reactive sputtering or chemical vapour depositing aluminum oxide onto a substrate.

In some embodiments, the interface molecule includes one or more of the amino acids selected from the group consisting of aspartic acid (Asp), glutamic acid (Glu), and gamma-carboxyglutamic acid (Gla).

In some embodiments, the interface molecule is a Vitamin K dependent protein, a fragment thereof containing a Gla domain, or a fragment thereof containing a modified Gla domain.

In some embodiments, the interface molecule and the biomolecule are formed as an engineered molecule such that the carboxy rich domain is included in a protein, a polypeptide, an antigen, an antibody, a carbohydrate, an aptamer or a lipid.

In some embodiments, the carboxy rich domain includes a Gla domain of a Vitamin K depend protein, or a fragment or derivative thereof, and the engineered molecule includes protein A, fragment B of protein A, or an IgG molecule.

In some embodiments, the interface molecule is a protein, a Gla domain of a protein, or a modified Gla domain of a protein in which one or more of the Gla residues are substituted with Glu, Asp, Glu-Glu, Glu-Asp, Asp-Glu or Asp-Asp, wherein the protein is selected from the group consisting of prothrombin, Fragment 1 of prothrombin, protein S, coagulation Factor IX, Factor X, Factor VII, protein C, matrix Gla protein, and bone Gla protein.

In some embodiments, the biomolecule is a member of a binding pair selected from the group consisting of antibody-antigen, antibody-hapten, enzyme-substrate, enzyme-receptor, toxin-receptor, protein-protein, avidin-biotin, aptamer-aptamer target, and drug receptor-drug.

The invention also extends to use of an interface molecule to refunctionalize an aluminum oxide surface for use in biomedical applications, wherein the interface molecule comprises a polypeptide having at least one carboxy rich domain providing at least 5 free carboxyl groups within a molecular volume of 2.2-25 $nm^3$, the free carboxyl groups being provided by amino acids containing two or more carboxyl groups, through which the interface molecule is capable of being immobilized to the aluminum oxide surface.

BRIEF DESCRIPTION OF THE DRAWINGS

FIG. 30A shows the engineered antibody in a solution with a mixture of proteins; FIG. 30B shows the binding of the engineered antibody to its specific antigen; FIG. 30C shows the binding of the engineered antibody-antigen complex through the carboxy rich domain to the aluminum oxide surface; and FIG. 30D shows the separation of the protein of interest from the mixture by removing the aluminum oxide surface from the solution. If the aluminum oxide surface is formed as a visual diagnostic device, the binding of the antigen is detected by a colour change in FIG. 30D. As an example, the Fab can be anti-albumin and the target protein can be albumin.

FIG. 32B shows the interface molecule on the aluminum oxide surface and the engineered antibody attached to the interface molecule through $Fab_1$. FIG. 32C shows the engineered antibody binding to an analyte antigen through $Fab_2$. Alternatively, the $Fab_2$ can be attached to a further biomolecule that functions as part of a binding pair such as an antibody or aptamer. For example $Fab_1$ can be anti-thrombin and $Fab_2$ can be anti-prostate specific antigen, while the analyte is prostate specific antigen.

In FIG. 33B, biomolecules are attached through the cross linking agent. The biomolecules are different antigens which are recognized by the different antibodies in a sample. For example, target molecules may be two different hormones, such as hCG and LH. If the underlying surface is aluminum oxide on a reflective layer to function as a visual assay, binding of the different antibodies generates multiple colour combinations depending on which antibodies are present in the sample. For example, 0 denotes no colour change for no antibody binding, 1 or 2 denoting colour change for binding of either antibody 1 or antibody 2, and 3 denoting colour change for binding of both antibody 1 and antibody 1. In other embodiments, the biomolecules may be antibodies, aptamers or a components of alternate binding pairs.

In FIG. 35A, aluminum is sputtered onto a surface in a pattern of lines using masking techniques known in the art. The aluminum is sputtered onto a thin film of tantalum on an underlying support, such as a slide. The aluminum can then be anodized to form a layer of aluminum oxide on a layer of tantalum oxide on a tantalum surface. Once anodizing is complete, the aluminum oxide strips are capable of producing interference colours, which change upon each addition of interface molecules, biomolecules and analytes binding to the biomolecules. Detection of the change in interface colours can be detected by the eye in the visible spectrum, and/or with suitable detectors, cameras etc. in the visible spectrum or outside the visible spectrum. In some embodiments the patterns such as these can be achieved by printing the interface molecules as lines or patterns on a continuous aluminum oxide film on an underlying reflective layer.

DETAILED DESCRIPTION

Figure 1:
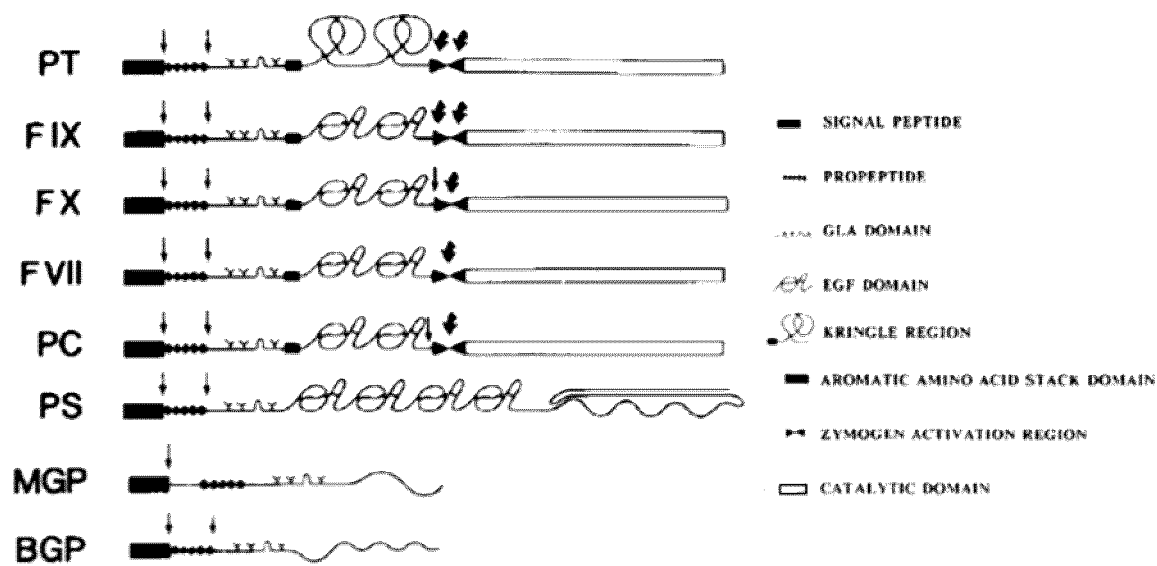
FIG. 1 depicts the structural domains of vitamin K-dependent proteins prothrombin (PT), factor IX (FIX), factor X (FX), factor VII (FVII), protein C (PC), protein S (PS), matrix Gla protein (MGP), and bone Gla protein (BGP). The legend identifies protein components. Proteolytic cleavage sites are shown with thin arrows when cleaving occurs to create the mature protein structure, and cleavage sites are indicated by thick arrows when linked to enzymatic activation. Image from Furie B and Furie BC (Furie and Furie, 1988).

Certain terms used herein and in the claims are defined and clarified hereinbelow.

The term "biomolecule" includes molecules that interact with a biological system. In general a biomolecule (or a biological molecule) is a term for molecules or ions that are present in organisms. Biomolecules include large macromolecules (or polyanions) such as proteins, carbohydrates, lipids and nucleic acids (aptamers), or derivatives or fragments thereof. Biomolecules also include small molecules such as primary metabolites, secondary metabolites, natural products and their derivatives. Biomolecules are usually endogenous, but may be exogenous. For example, pharmaceutical drugs may be natural products or semisynthetic (biopharmaceuticals) or they may be totally synthetic, and as such are included in the term biomolecules. Biomolecules also extends to synthetic proteins, polypeptides, and peptides, synthetic DNA or RNA, synthetic lipids and synthetic carbohydrates.

The terms "alumina" and "aluminum oxide" are used synonymously herein, and includes an oxide formed on the surface of aluminum or an aluminum metal alloy, whether the oxide is native or formed, for example by sputtering or by anodizing to provide an aluminum oxide. The aluminum oxide surface may be formed on a substrate or a support, such as on a particle, powder, bead, magnetic bead or particle, thin film, slide, strip, filter, or coating. The aluminum oxide surface may be formed by sputtering, RF sputtering, reactive sputtering, chemical vapour deposition, evaporating, casting, or extruding aluminum metal or an aluminum alloy, and may be further anodized to provide a porous anodized aluminum oxide surface.

The terms "bioidentity" and "biological identity" are used synonymously to refer to the structural and chemical property of a biomolecule that make it recognizable or specific to binding to other biomolecules, cells or tissues. For example, when an antigen is immobilized it is said to have retained its bioidentity if an antibody that was developed to it in an animal model, in vitro system, or computational model, binds to it with the same specificity and sensitivity as it would if it were free in solution. As used herein, bioidentity does not necessarily require retained biological activity in a biomolecule, for example in an enzyme, it is sufficient that the biomolecule is still recognized.

The term "domain" refers to a group of amino acids within a protein or polypeptide which is identifiable by function, properties or structure from other parts of the protein or polypeptide.

The terms "immobilized" or "immobilize" as used herein refers to the attachment or adherence of one or more interface molecules to the aluminum oxide surface, whether or not through chemical bonding.

The terms "covalent binding", "covalent bonding" and "cross-linking" are used herein to refer to the formation of covalent bonds between the interface molecule and the biomolecule. Typically, when the biomolecule is a polypeptide, the interface molecule is covalently bonded through a cross-linking agent. Alternatively, when the interface molecule is engineered to include the biomolecule, the covalent binding is through peptide bonds.

The term "polypeptide" refers to chains of amino acids held together by peptide bonds, and as used herein includes proteins, whether natural or engineered, fragments of such proteins, and amino acid sequences derived from such proteins or fragments.

The term "sample" as used herein includes any biological or environmental material suspected of containing one or more analytes of interest, and includes a sample which lacks the analyte such that the test for the analyte is negative. Biological samples include, for example, bodily fluids and organic materials such as foodstuffs. A bodily fluid includes, for example, whole blood, plasma, serum, sputum, cerebrospinal fluid, pleural fluid, tissue, fecal material and the like. Environmental samples include, for example, soil, sludge, water and the like. The sample can be processed, for example centrifuged, extracted, and/or lysed if cells are present. Alternatively, the sample can be directly placed in contact with the diagnostic device.

In accordance with the invention, an aluminum oxide surface is refunctionalized with an interface molecule capable of being immobilized on the surface, for use in biomedical applications. In some embodiments, the interface molecule can be activated by attaching to a cross linking agent, which can than be used to bind to analytes of interest in test sample. In other embodiments, the interface molecule can be attached to a biomolecule, which can then be used (directly or indirectly) to bind to analytes of interest in a test sample. In some embodiments, the biomolecule is covalently bonded to the interface molecule, either with cross linking agents, or by covalent bonds such as peptide bonds. The interface molecule and the biomolecule may be engineered together as an interface complex. In other embodiments, the biomolecule may be an engineered antibody, for example having one antigenic determinant specific to the interface molecule and a second antigenic determinant specific to an analyte of interest in a test sample, or to another biomolecule. In other embodiments, the biomolecule may be an engineered antibody attached to the interface molecule though an Fc fragment of the antibody and having Fab fragments specific to the analyte of interest.

The interface molecule includes a polypeptide having at least one carboxy rich domain providing at least 5 free carboxyl groups within a molecular volume of 2.2-25 nm$^3$. The free carboxyl groups are provided by amino acids containing two or more carboxyl groups, through which the interface molecule is immobilized to the aluminum oxide surface. The attached biomolecule retains its biological identity when attached to the interface molecule.

For clarity, as defined herein and in the claims, the complex resulting for an interface molecule attached to a biomolecule excludes an end product which is a vitamin K dependent protein such as prothrombin.

In some embodiments, the carboxy rich domain provides at least 10 free carboxyl groups within a molecular volume of 2.2-25 nm$^3$; or at least 20 free carboxyl groups within a molecular volume of 2.2-25 nm$^3$; or at least 10 free carboxyl groups within a molecular volume of 7.0-20 nm$^3$, or at least 20 free carboxyl groups within a molecular volume of 7.0-17 nm$^3$.

i) Interface Molecules or Interface Complexes with Biomolecules

In accordance with the invention, interface molecules having a particularly high affinity to the aluminum oxide surface through one or more carboxy rich domains, are immobilized on an aluminum oxide surface, for instance as a continuous or discontinuous coating, as delineated spots or lines, or as an array. The interface molecule can be immobilized as a coating on the aluminum oxide surface from a solution of the interface molecule in a suitable solvent, followed by removing the solvent. In general, the interface molecule includes one or more of the amino acids aspartic acid (Asp), glutamic acid (Glu) and gamma-carboxyglutamic acid (Gla) to provide the carboxy rich domain(s). Examples of interface molecules are the Vitamin K dependent proteins, fragments thereof containing the carboxy rich Gla domain, fragments thereof containing a modified Gla domain, or synthetic peptides providing one or more carboxy rich domains. The interface molecule and the biomolecule may be formed as an engineered molecule such that the carboxy rich domain is included in a protein, a polypeptide, an antigen, an antibody, a carbohydrate, an aptamer or a lipid. For example, the carboxy rich domain may include one or more of the Gla domains of a Vitamin K dependent protein, or a fragment or a derivative thereof, and the engineered molecule may include a biomolecule such as protein A, fragment B of protein A, or an IgG molecule.

In embodiments in which the one or more carboxy rich domains are provided in the interface molecule as a synthetic peptide, the carboxyl group-containing amino acids are positioned and spaced in the synthetic peptide to ensure that sufficient free carboxyl groups are exposed on the surface of the folded synthetic peptide such that they are available for immobilizing to the aluminum oxide surface. The ability to fold in a manner to expose the free carboxyl groups on the surface of the folded synthetic peptide can readily be confirmed by molecular models, as demonstrated in the examples which follow.

The size of the interface molecule varies with the particular application for the immobilized interface and biomolecule. For instance, when the biomolecule is an engineered antibody having an interface molecule incorporated in the Fc fragment, the interface molecule is preferably sized to limit steric hindrance. For example, for an antibody having about a 50 kD sized heavy chain, the interface molecule preferably has a smaller size, such as less than about 30 kD, and each of one or more carboxy rich domain portions, Gla domain portions, or modified Gla domain portions of the interface molecule provides at least 5 free carboxyl groups within about 50 consecutive amino acids. Examples of this interface molecule sizing with IgG biomolecules is shown in Examples 14 and 16-19 which follow.

The distance from the aluminum oxide surface can be controlled by varying the size of the interface molecule. Prothrombin holds the immobilized entity about 10 nm off the surface while the Fragment 1 domain of prothrombin holds hold the immobilized entity about 3 nm off the surface. Suitable linkers can be used to vary the distance the molecules are held off the surface from about 1 nm to about 40 nm.

Figure 29:
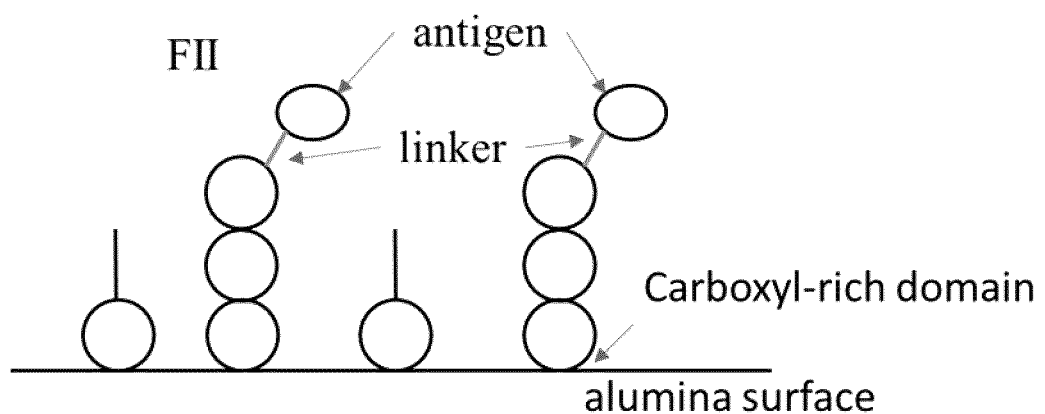
FIG. 29 is a schematic drawing showing an aluminum oxide surface with both Fragment 1 of prothrombin and prothrombin (FII) as two types of interface molecules bound to the surface through the Gla domain. A cross linking agent such as glutaraldehyde is added for binding a biomolecule, such as an antigen. This device uses one type of interface molecule (Frag 1) to act as a spacer between the other interface molecule (FII) to reduce factors such as steric hindrance. The antigen, and the antibody specific to the antigen (not shown), have less steric hinderance for attaching to the interface molecule (FII) most distant from the surface. For example, the immobilized antigen can be the Hep B virus antigen, and a linker capping agent (ex. lysine) can be added after binding of the antigen to prevent non-specific protein binding.
Figure 30A:
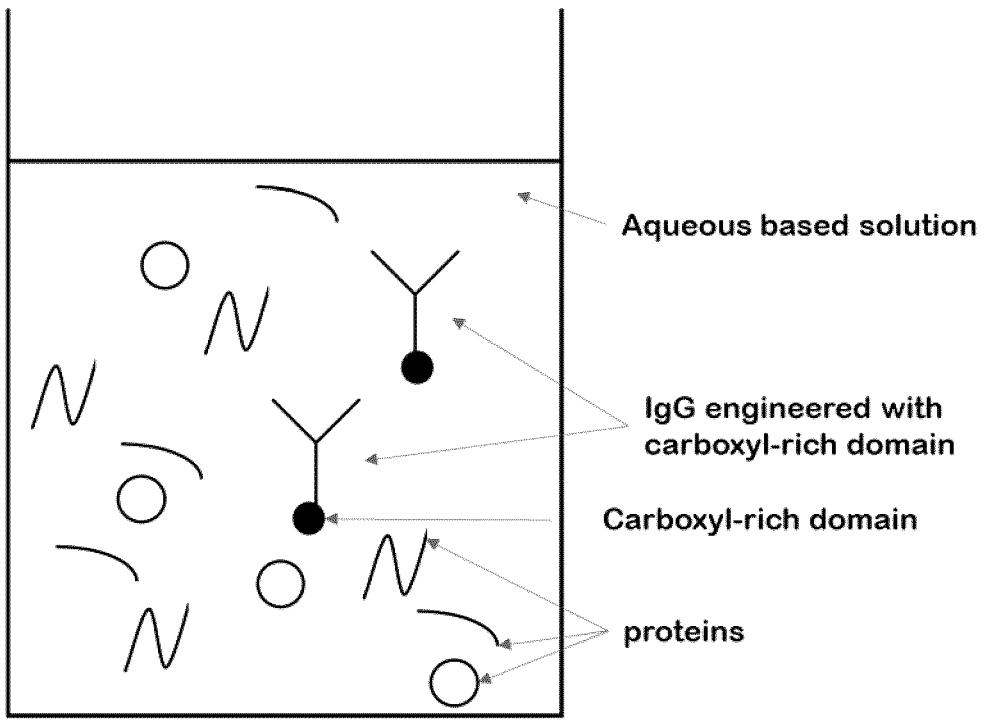
FIGS. 30A-30D are schematic drawings showing the use of an interface complex including an interface molecule and an antibody. The complex is an engineered antibody with a carboxy rich domain on the Fc terminus, or an antibody which is Fc conjugated, via the carboxyl terminus, to a carboxy rich domain, used to capture antigens as analytes in a test sample. An example of an engineered antibody of this type is the Gla domain of a vitamin K dependent protein linked to the Fc terminus of an IgG antibody. The antigens are separated from the solution by contacting with an aluminum oxide surface, such that the carboxy rich domain of the engineered antibody, bound to the antigens, binds to the alumina surface.
Figure 30B:
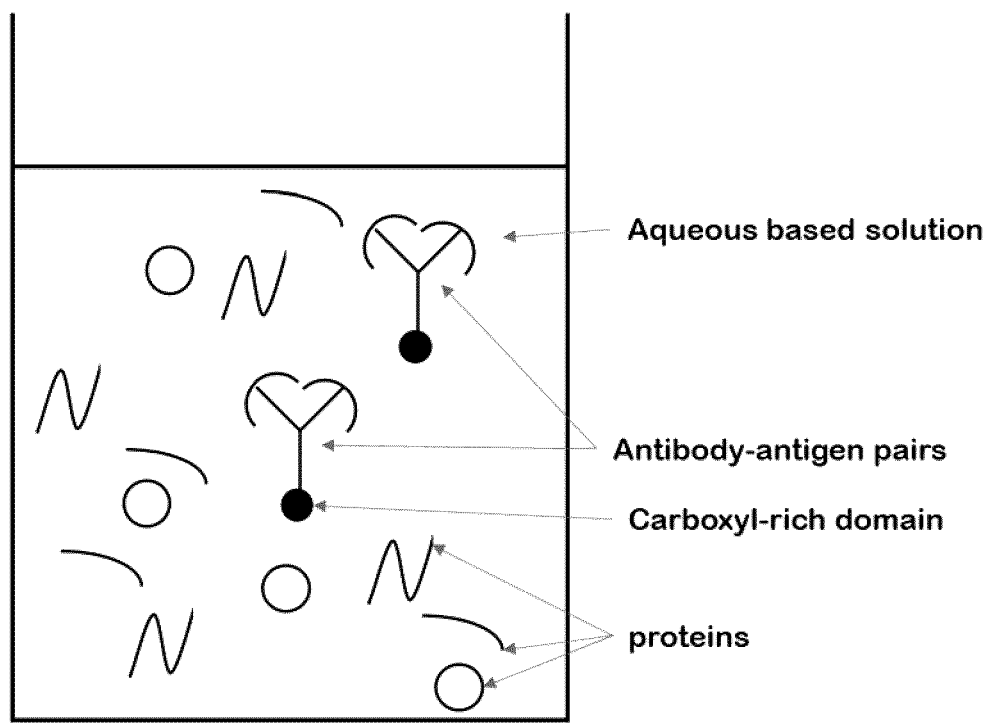
Figure 30C:
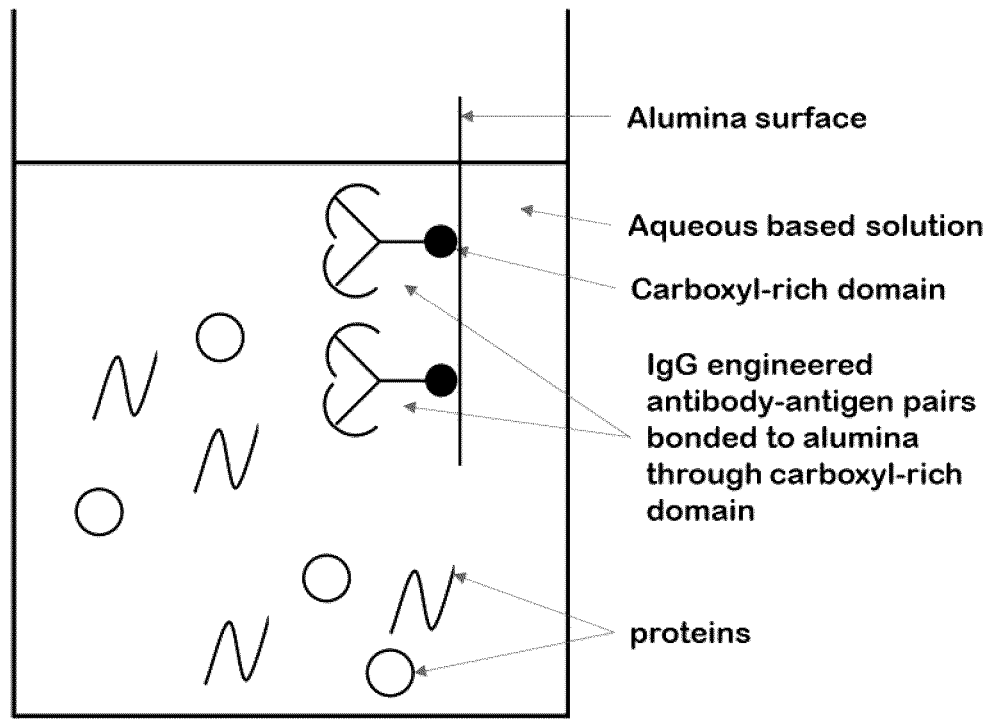
Figure 30D:
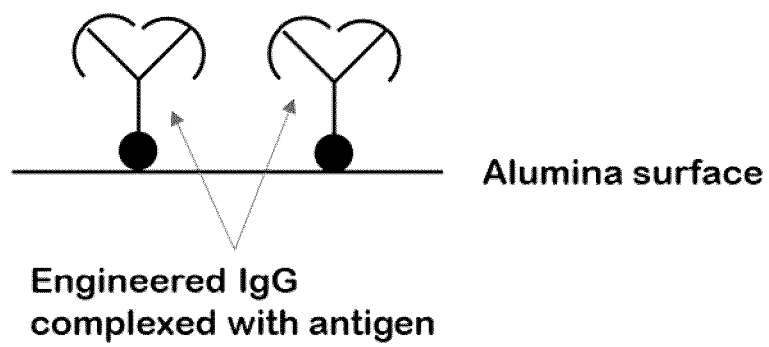
Figure 31A:
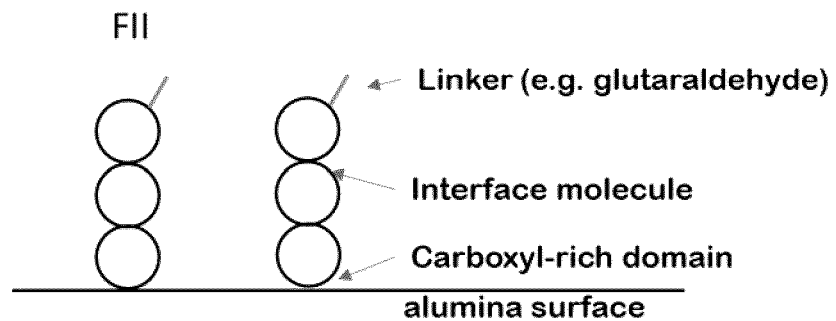
FIGS. 31A-31D are schematic drawings showing an aluminum oxide surface having immobilized thereon an interface molecule such as prothrombin (FII). The FII molecule is modified with a cross linking agent such as glutaraldehyde, as shown in FIG. 31A. The surface is immersed in an sample such urine in FIG. 31B. If there is analyte protein in the sample, it binds to the glutaraldehyde on the interface molecule, as shown in FIG. 31C. Removing the surface from the sample removes protein bound to the interface molecule through the cross linking agent, as shown in FIG. 31D. If the aluminum oxide surface is formed as a visual diagnostic device, the binding of the protein is detected by a colour change in FIG. 31D.
Figure 31B:
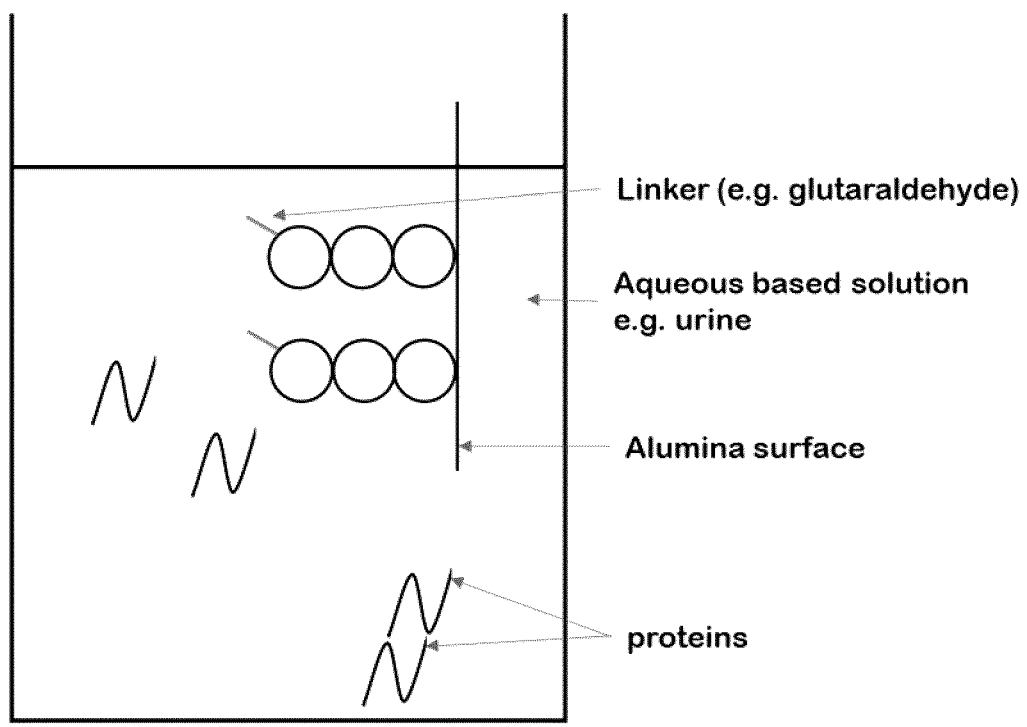
Figure 31D:
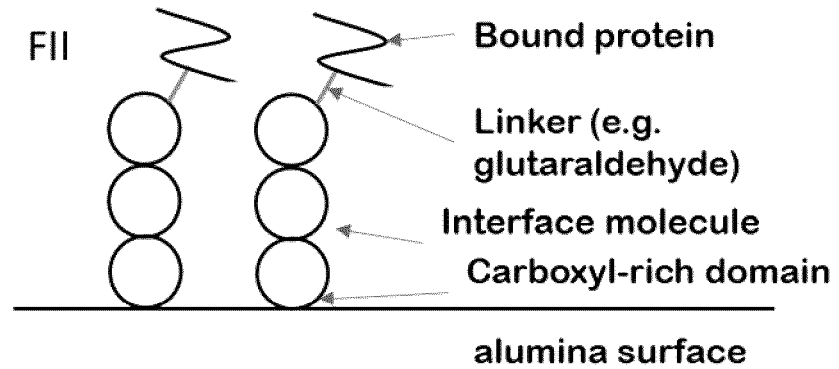
Figure 31C:
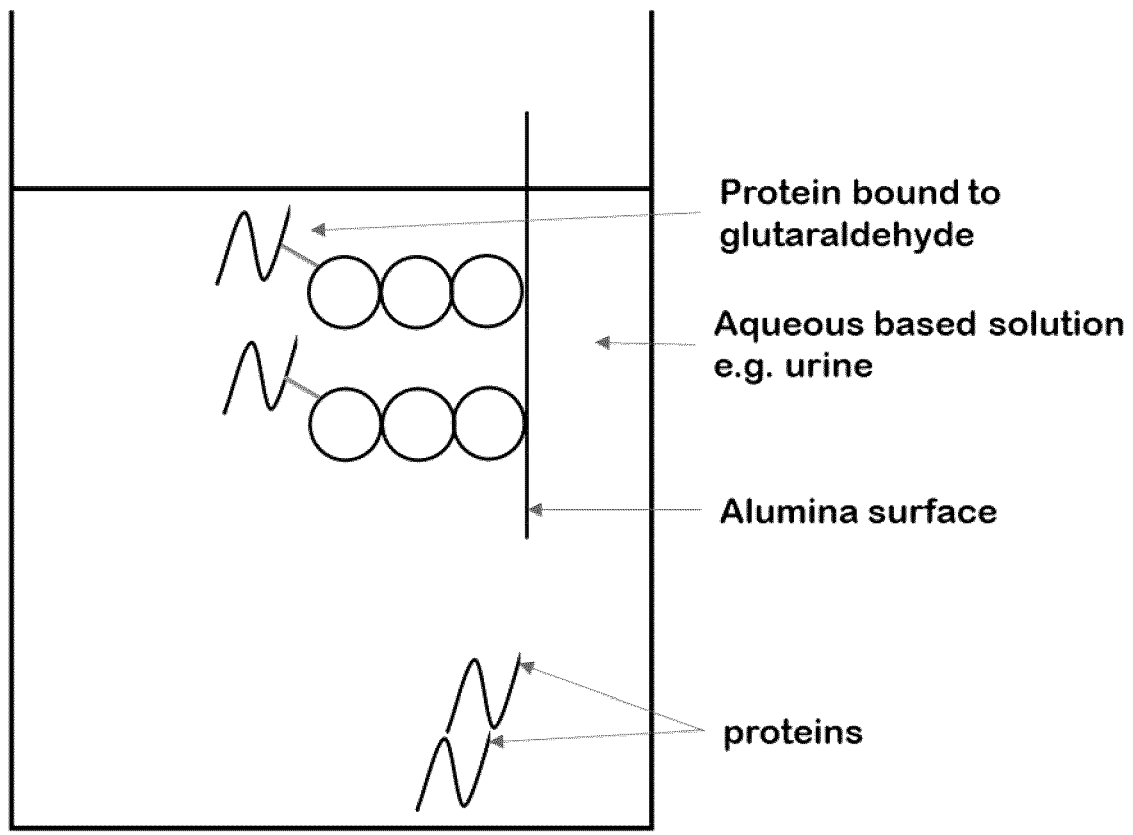
Figure 32A:
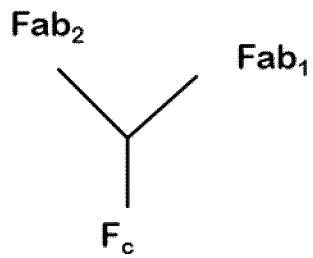
FIGS. 32A-32C are schematic drawings showing an interface complex including an interface molecule and an antibody as an engineered antibody. The interface molecule, such as Fragment 1 of Factor II is immobilized on the aluminum oxide surface. An antibody is engineered with two distinct Fab antigenic determinants, $Fab_1$ and $Fab_2$, as shown in FIG. 32A. The engineered antibody can be made through genetic engineering or wet chemistry, by techniques known in the art. $Fab_1$ is specific to the interface molecule in order to bind to the interface molecule (for example the antithrombin component of antiprothrombin), while $Fab_2$ is specific to an analyte of interest such as an antigen.
Figure 32B:
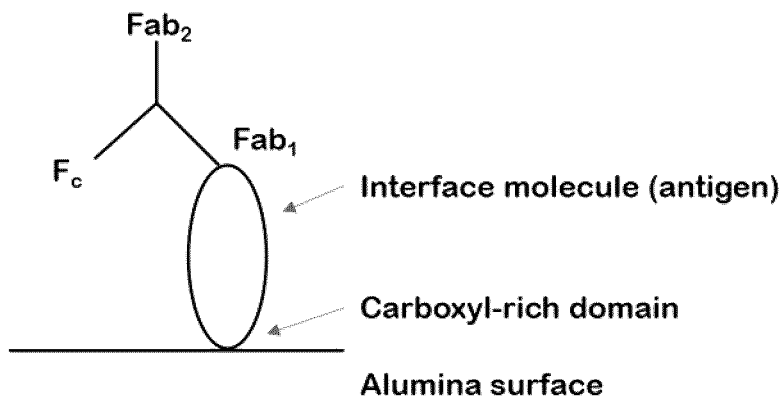
Figure 32C:
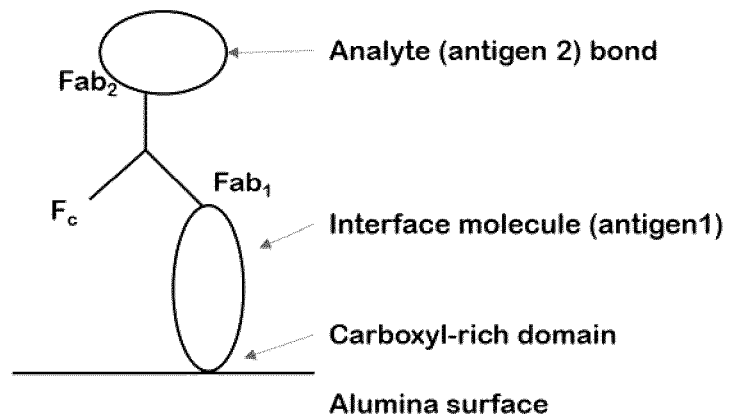
Figure 33A:
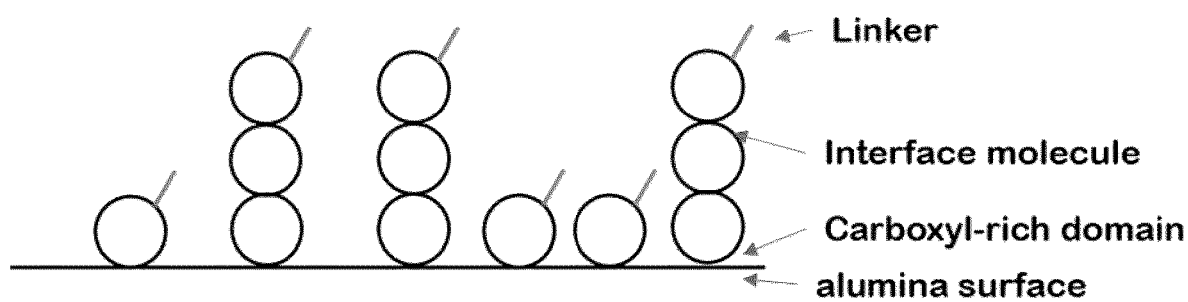
FIGS. 33A and 33b are schematic drawings showing the simultaneous use of two different sized interface molecules (high and low) bound to an aluminum oxide surface through a carboxy rich domain. This configuration allows two different biomolecules to be linked to the interface molecule, for example through a cross linking agent such as an aptamer (FIG. 33A). The linker can be added in bulk solution for one interface molecule, and in a separate solution of the other interface molecule. For example the high interface molecule can be prothrombin, and the low interface molecule can be Fragment 1 of Factor II.
Figure 33B:
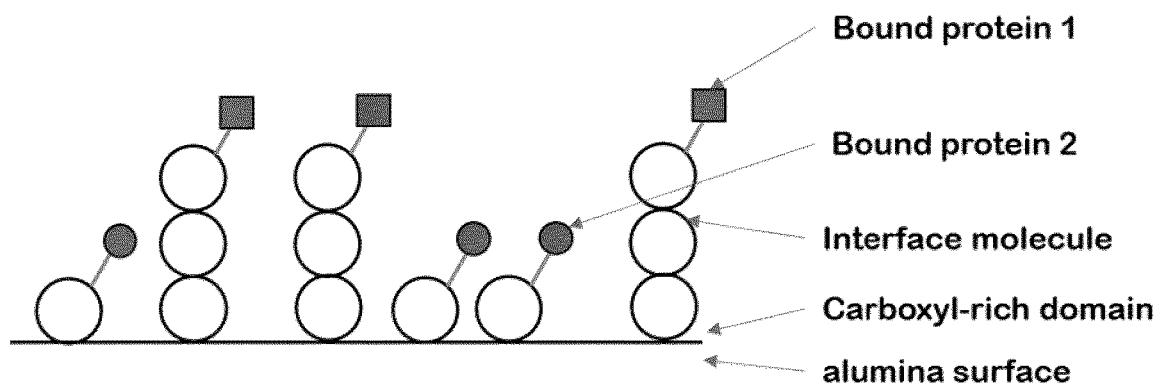
Figure 34A:
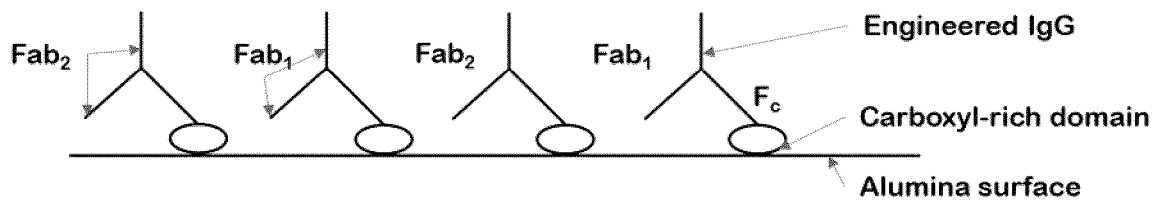
FIGS. 34A and 34B are schematic drawings showing binding of polyclonal engineered IgG to the aluminum oxide surface. The IgG molecules are engineered with a carboxy rich domain formed at the carboxyl terminus of the Fc fragment, for binding to the aluminum oxide surface. The Fab fragments are illustrated as $Fab_1$ and $Fab_2$ for binding to different epitopes of the antigen of interest (orientation 1 or orientation 2 being shown in FIG. 34B). In this manner, the Fab fragments are able to bind specifically to the antigen they were developed for. By using a polyclonal antibody, the binding is faster as the orientation of the antibody is not a significant factor. For example, $Fab_1$ can be monoclonal-1 for prostate specific antigen (specific site/orientation) and $Fab_2$ can be monoclonal-2 for prostate specific antigen (specific site/orientation), while the analyte is prostate specific antigen.
Figure 34B:
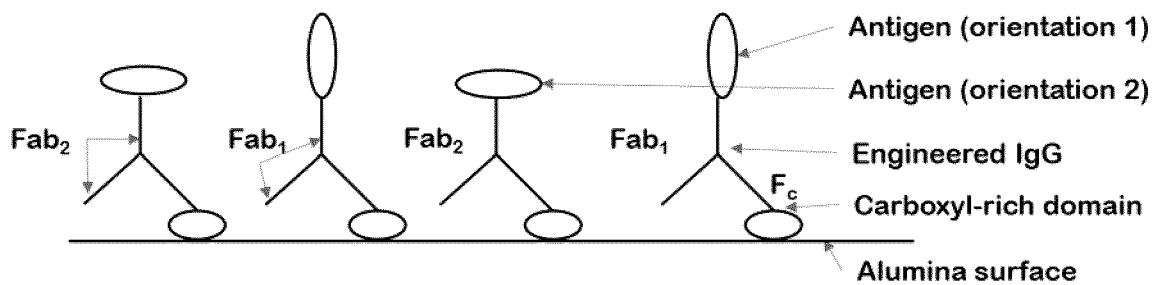
Figure 35A:
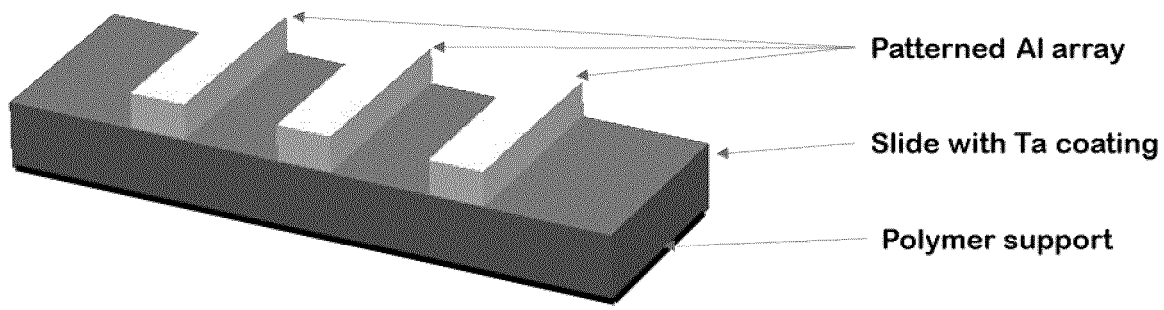
FIGS. 35A and 35B are schematic drawings showing two embodiments for patterning the interface molecules on an aluminum oxide surface.
Figure 35B:
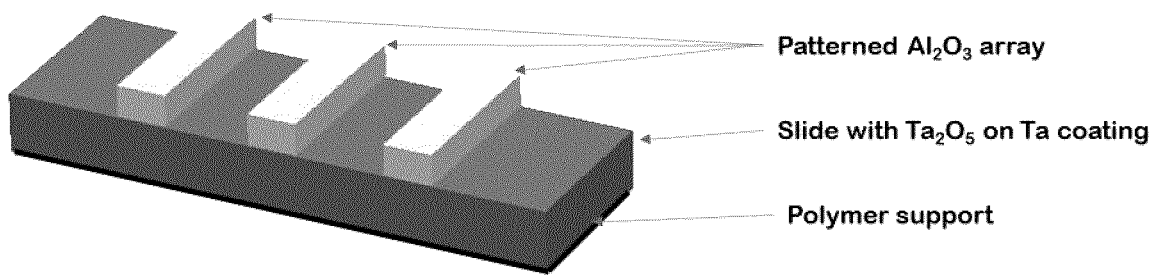

The interface molecule can include different types of interface molecules spaced on the aluminum oxide surface, for example as shown in FIG. 29, to reduce steric hindrance. As shown in FIG. 29, prothrombin is spaced apart from Fragment 1 of prothrombin. The prothrombin is bound to a biomolecule such as an antigen.

The interface molecule immobilized on the aluminum oxide surface can be activated with a cross linking agent to attach to an analyte of interest (as in FIG. 31), or for attaching to a biomolecule. Alternatively, the biomolecule and the interface molecule are preassembled as a complex using cross linking agents, and the complex is then immobilized on the aluminum oxide surface. Alternatively, the interface molecule and the biomolecule are formed through genetic engineering or wet chemistry, for example by forming antigens or antibodies in large scale with appropriate binding sequences of a carboxy rich domain (e.g., the first 32 amino acids of human prothrombin: Ala-Asn-Thr-Phe-Leu-Gla-Gla-Val-Arg-Lys-Gly-Asn-Leu-Gla-Arg-Gla-Cys-Val-Gla-Gla-Thr-Cys-Ser-Tyr-Gla-Gla-Ala-Phe-Gla-Ala-Leu-Gla-XXX see SEQ ID NO:1)) attached to the end of the molecule.

In some embodiments, the interface molecule is provided on the aluminum oxide surface as a continuous or discontinuous coating, as delineated spots or lines, or as an array.

In some embodiments the aluminum oxide surface is provided on a substrate in the form of a particle, powder, thin film, slide, strip, filter, bead, magnetic bead, magnetic particle, or coating.

There are several Gla containing proteins including the Vitamin K dependent proteins: Factor II, Factor VII, Factor IX, Factor X, protein C, protein S, protein Z, osteocalcin, matrix Gla protein (MGP), bone Gla protein (BGP), GAS6 periostin, two transmembrane Gla proteins (TMGPs), and two proline-rich Gla-proteins (PRGPs). The structures of some of these Gla domain proteins are shown in FIG. 1. Sequence listings are provided for Factor II (prothrombin) in SEQ ID NO. 1, Factor IX in SEQ ID NO. 2, and Protein S in SEQ ID NO. 3. The charge to mass ratios of each protein plays a key role in how it diffuses to the surface of a substrate at low concentrations. The inventor has determined that the number, location and density of the free carboxyl groups is important to the binding of the proteins to the aluminum oxide surface. In particular, as set out below, the inventor established that the volume of the carboxy rich domain and the density of free carboxyl groups (—COOH) in the carboxy rich domain of the interface molecule are factors that determine the binding of the interface molecule to the aluminum oxide surface.

Figure 2:
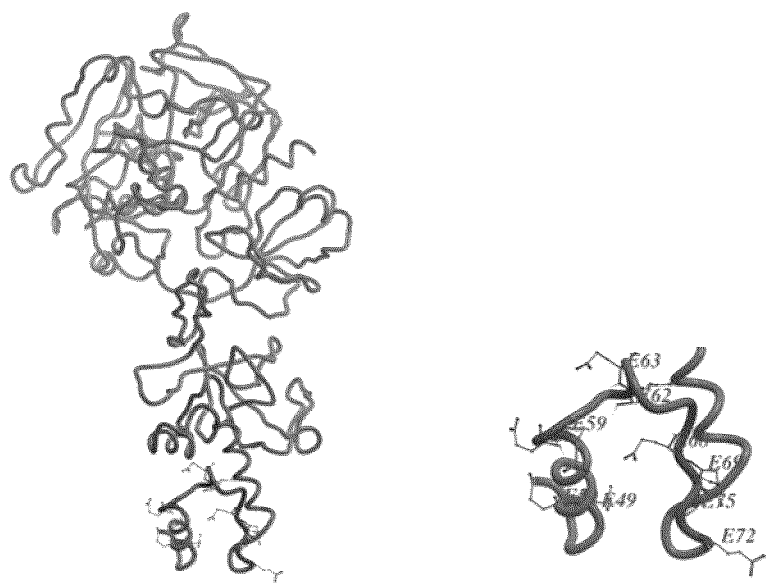
FIG. 2 shows the 3D structure of prothrombin. There are 10 Gla residues located at sites 6, 7, 14, 16, 19, 20, 25, 26, 29, and 32 on the protein (UnitProt Consortium, 2017a). This forms an 8.3 nm$^3$ carboxyglutamic domain (carboxy rich Gla domain) at the base of the structure where binding to the alumina surface occurs.

The volume of the Gla domain of Fragment 1 of prothrombin was established using computer software. I-Tasser generated models were opened in Molsoft ICM-Pro. The protein region of interest was selected and the other regions hidden. Under the display settings, the option to measure the distance between two atoms was selected. Two points were then selected to generate length, width, and height dimensions for the area of interest. The product of these dimensions provided the volume of the Gla domain or charged region, depending on the molecule. The same software was used to then establish the volumes and density of the free carboxyl groups for the carboxy rich domains of naturally occurring proteins, protein S, FIX and Fragment 1 of bovine prothrombin, as shown in Table 1 below. Likewise, the volumes and free carboxyl group densities were established for a range of synthetic carboxy rich domains based on the base structure of the Gla domain of prothrombin, as shown in Table 1, and as more fully described hereinbelow. These volumes ranged from 2.2 to 17 nm$^3$ with free carboxyl group densities from 1.15 to 9.09/nm$^3$. The volume range was found to be bracketed by the naturally occurring FIX (17 nm$^3$) and the fusion protein of two naturally occurring domains, the Gla domain of prothrombin and the Fragment B domain from protein A (2.2 nm$^3$). The synthetic carboxy rich domain volumes fell between these two proteins. The density range is bracketed by a synthetic carboxy rich domain (FII-frag1-Asp described below, at 1.15 COOH/nm$^3$) and the fusion protein of two naturally occurring domains, the Gla domain of prothrombin and the Fragment B domain from protein A (9.09 COOH/nm$^3$), with other carboxy rich domain examples falling between these proteins. Density multiplied by volume in Table 1 provides the number of free carboxyl groups in the carboxy rich domain. This ranges from 10-24 free carboxyl groups. A comparison of the synthetic protein constructs (see FIGS. 5-14) to Fragment 1 of Factor II (FIG. 2 and FIGS. 15-16) shows that the basic structure is maintained with the carboxyl groups exposed in a general cluster. This indicates that the synthetic constructs provide a carboxy rich domain for binding to aluminum oxide surfaces in much the same manner as do the natural vitamin K dependent molecules.

Based on examples to follow, and as further established including the molecular modelling work, the carboxy rich domain for binding to aluminum oxide surfaces provides at least 5 free carboxyl groups within a molecular volume of 2.2-25 $nm^3$, or at least 10 free carboxyl groups within a molecular volume of 2.2-25 $nm^3$, or at least 20 free carboxyl groups within a molecular volume of 2.2-25 $nm^3$, or at least 10 free carboxyl groups within a molecular volume of 2.2-17 $nm^3$, or at least 20 free carboxyl groups within a molecular volume of 2.2-17 $nm^3$, or at least 10 free carboxyl groups within a molecular volume of 7.0-17 $nm^3$, or at least 20 free carboxyl groups within a molecular volume of 7.0-17 $nm^3$.

Human prothrombin contains 10 γ-carboxyglutamic acid (Gla) residues in the $NH_2$-terminal domain. The Gla residues occur in adjunct pairs or in close proximity to each other (residues 6, 7, 16, 19, 20, 25, 26, 29, 32) (Walz DA et al., 1977; UnitProt Consortium, 2017a). These 10 Gla residues, which have 20 free carboxyl groups, occupy a space of 8.3 $nm^3$. This gives a density of 2.4 carboxyl groups per $nm^3$. Prothrombin has high affinity metal binding sites for $Ca^{2+}$. These binding sites are formed by two Gla residues in the polypeptide chain, which share a single bound metal ion. An intermolecular bridge forms, which stabilizes the tertiary structure of the protein. The high concentration of Gla residues at the $NH_2$-terminal domain in prothrombin, when used as an interface molecule with alumina surfaces, provides consistent binding to aluminum oxide with a specific orientation.

FIG. 2 shows the 3-dimensional structure of prothrombin, which illustrates the localization of the Gla domains to a confined (8.3 $nm^3$) portion of the protein structure. As an interface molecule herein, prothrombin is found to bind to an aluminum oxide surface at the Gla domain because Gla has a high affinity to the alumina surface relative to other amino acids. Prothrombin has a molecular weight of 72,000 Da, an isoelectric point in the range of 4.7-4.9, and a dissociation constant of ~1 μmol/L (Bajaj et al., 1975; Kotkow et al., 1993; Mann, 1976; UnitProt Consortium, 2017a).

Human prothrombin is a three-domain protein consisting of Fragment 1, Fragment 2 and thrombin. The Gla residues (10) are all located in Fragment 1. It consists of 155 amino acid residues (human). The Gla residues are all located in the first 32 amino acid residues. This moiety thus has a high affinity for alumina substrates. These 10 Gla residues, which have 20 free carboxyl groups, occupy a space of 8.3 $nm^3$. This gives a density of 2.4 carboxyl groups per $nm^3$.

The carboxy rich domain of the interface molecule can be provided by modifying the Gla domain of a Vitamin K dependent protein, or of a fragment of a Vitamin K dependent protein, such as set out below and in the Examples which follow. The modification can be achieved by genetic engineering techniques well known to persons skilled in the art, or by wet chemistry.

Fragment 1 of Factor II can be modified with a dicarboxyl amino acids such as aspartic acid. This is shown in FIG. 5 where there are 10 Asp residues located at sites 6, 7, 14, 16, 19, 20, 25, 26, 29, and 32 in the protein. This forms an 8.7 $nm^3$ carboxy rich domain at the base of the structure where binding to the alumina substrate occurs. These 10 Asp residues, which have 10 free carboxyl groups, occupy a space of 8.7 $nm^3$. This gives a density of 1.15 carboxyl groups per $nm^3$. The surface charge map of the 3D structure of a modified Fragment 1 of Factor II (FIG. 6) shows the concentration of surface charge at the carboxy rich domain that facilitates binding to alumina.

Fragment 1 of Factor II can be modified with a pair of dicarboxyl amino acids such as aspartic-aspartic acid. In FIG. 7 there are 10 (Asp-Asp) residues in place of Gla residues located at sites 6, 7, 14, 16, 19, 20, 25, 26, 29, and 32 on the protein. This forms a 7.7 nm³ carboxy rich domain at the base of the structure where binding to the alumina substrate occurs. These 20 Asp residues, which have 20 free carboxyl groups, occupy a space of 8.7 nm³ with a carboxyl density of 2.60 carboxyl groups per nm³. The surface charge map of the 3D structure of a modified Fragment 1 of Factor II (FIG. 8) shows the concentration of surface charge at the carboxy rich domain which facilitates binding to alumina.

Figure 9:
Figure 10:
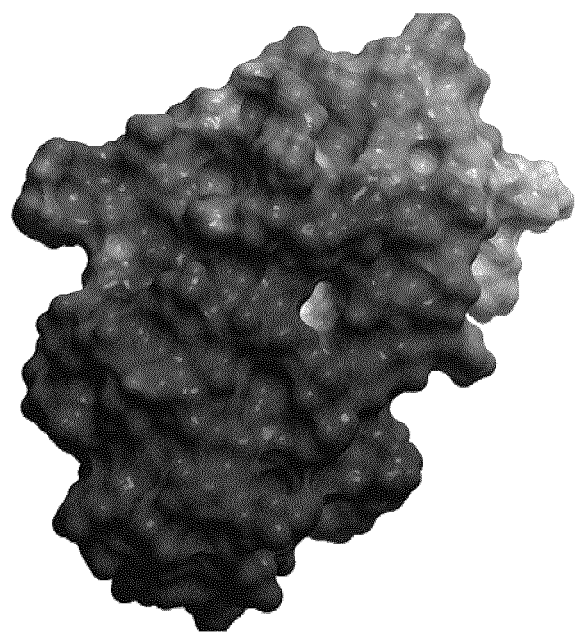

Fragment 1 of Factor II can be modified with a pair of dicarboxyl amino acids such as aspartic-glutamic acid. In FIG. 9 there are 10 (Asp-Glu) residues in place of Gla residues located at sites 6, 7, 14, 16, 19, 20, 25, 26, 29, and 32 on the protein. This forms a 8.5 nm³ carboxy rich domain at the base of the structure where binding to the alumina substrate occurs. These 10 Asp-Glu residues, which have 20 free carboxyl groups, occupy a space of 8.5 nm³ with a carboxyl density of 2.35 carboxyl groups per nm³. The surface charge map of the 3D structure of a modified Fragment 1 of Factor II (FIG. 10) shows the concentration of surface charge at the carboxy rich domain which facilitates binding to alumina.

Figure 11:
Figure 12:
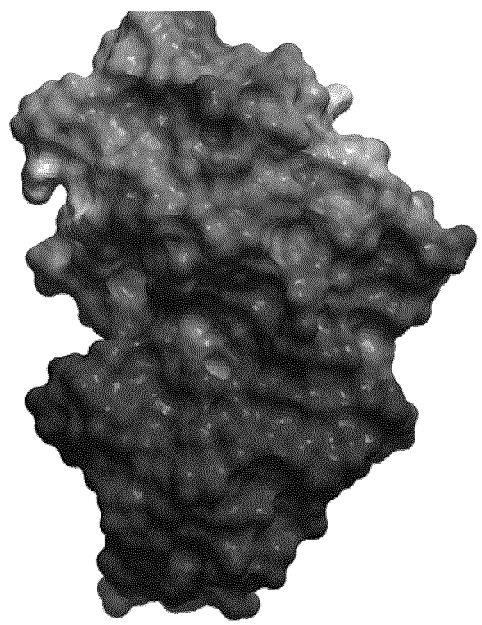

Fragment 1 of Factor II can be modified with a pair of dicarboxyl amino acids such as glutamic-aspartic acid. In FIG. 11 there are 10 (Glu-Asp) residues in place of Gla residues located at sites 6, 7, 14, 16, 19, 20, 25, 26, 29, and 32 on the protein. This forms a 12.5 nm³ carboxy rich domain at the base of the structure where binding to the alumina substrate occurs. These 10 Glu-Asp residues, which have 20 free carboxyl groups, occupy a space of 12.5 nm³ with a carboxyl density of 1.60 carboxyl groups per nm³. The surface charge map of the 3D structure of a modified Fragment 1 of Factor II (FIG. 12) shows the concentration of surface charge at the carboxy rich domain that facilitates binding to alumina.

Figure 13:
Figure 14:
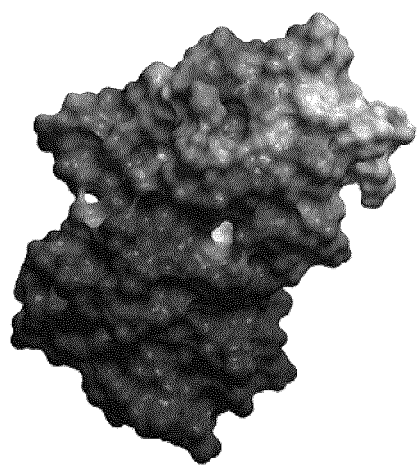

Fragment 1 of Factor II can be modified with a pair of dicarboxyl amino acids such as glutamic-aspartic acid. In FIG. 13, there are 10 (Glu-Glu) residues in place of Gla residues located at sites 6, 7, 14, 16, 19, 20, 25, 26, 29, and 32 on the protein. This forms a 11.8 nm³ carboxy rich domain at the base of the structure where binding to the alumina substrate occurs. These 10 Glu-Glu residues, which have 20 free carboxyl groups, occupy a space of 11.8 nm³ with a carboxyl density of 1.69 carboxyl groups per nm³. The surface charge map of the 3D structure of a modified Fragment 1 of Factor II (FIG. 14) shows the concentration of surface charge at the carboxy rich domain that facilitates binding to alumina.

Figure 15:
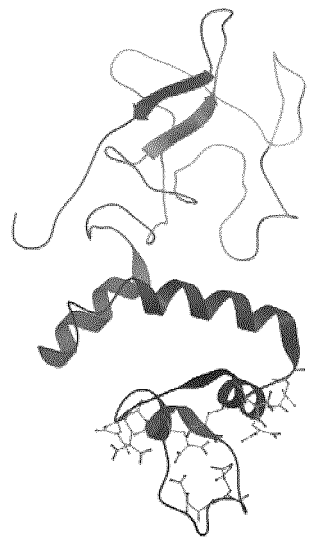
Figure 16:
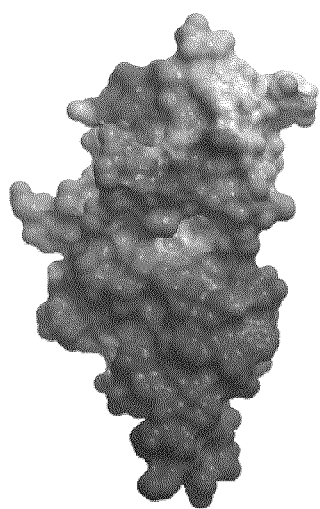

Bovine prothrombin is a three-domain protein consisting of Fragment 1, Fragment 2 and thrombin. FIG. 15 shows that the Gla residues (10) are all located in Fragment 1. It consists of 156 amino acids. The Gla residues are all located in the first 33 amino acid residues. This moiety has a high affinity for alumina substrates. These 10 Gla residues, which have 20 free carboxyl groups, occupy a space of 7.0 nm³. This gives a density of 2.86 carboxyl groups per nm³. The surface charge map of the 3D structure of bovine Fragment 1 of Factor II (FIG. 16) shows the concentration of surface charge at the carboxy rich domain that facilitates binding to alumina.

The interface molecule and the biomolecule can be formed as an engineered molecule, by genetic engineering techniques well known to persons skilled in the art, in a manner such that the carboxy rich domain is included in a protein, a polypeptide, an antigen, an antibody, a carbohydrate, an aptamer or a lipid. For example, Fragment 1 of human Factor II, or a fragment of a Vitamin K dependent protein containing the Gla domain, can be added to the carboxyl terminus of an IgG heavy chain to provide a carboxy rich domain at the base of the IgG structure, allowing binding of the engineered antibody to an alumina substrate. Similarly, synthetic antigens can be produced for immunoassays by adding a carboxy rich domain to a sequence of an antigen of interest. For example, there are 5-7 serotypes of Dengue virus, and synthetic antigens specific to each serotype can be engineered with the carboxy rich domain. When placed in a multiplexed pattern on the aluminum oxide surface, the disease can be rapidly diagnosed.

Figure 17:
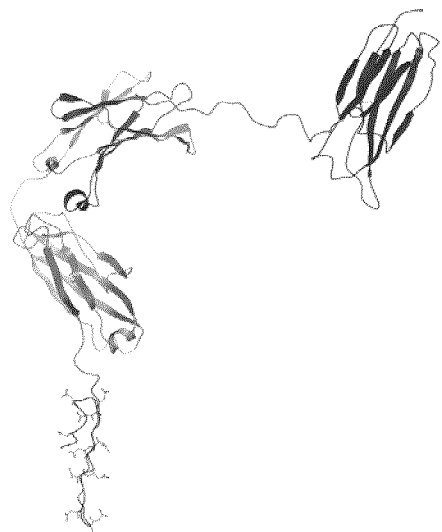
Figure 18:
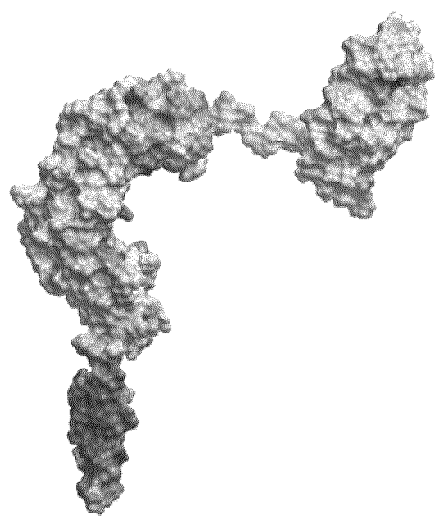

A modified (Asp in place of Gla) Fragment 1 of human Factor II can be added to the carboxyl terminus of an IgG heavy chain as shown in FIG. 17. There are 10 Asp residues in place of Gla residues located at sites 6, 7, 14, 16, 19, 20, 25, 26, 29, and 32 on the modified Fragment 1 protein. This forms a 3.6 nm³ carboxyl rich domain at the base of the IgG structure allowing binding to an alumina substrate. This results in a domain with a density of 3.03 carboxyl groups per nm³. The surface charge map of the 3D structure of a modified (Asp in place of Gla) Fragment 1 of human Factor II added to the carboxyl terminus of an IgG heavy chain (FIG. 18) shows the concentration of surface charge at the carboxy rich domain that facilitates binding to alumina.

Figure 19:
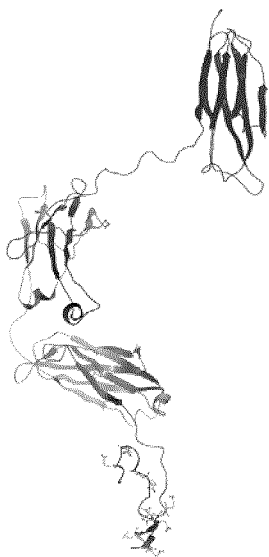
Figure 20:
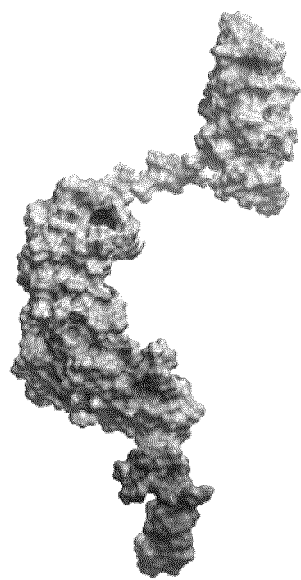

A modified (Glu in place of Gla) Fragment 1 of human Factor II can be added to the carboxyl terminus of an IgG heavy chain as shown in FIG. 19. There are 10 Glu residues in place of Gla residues located at sites 6, 7, 14, 16, 19, 20, 25, 26, 29, and 32 on the protein. This forms a 3.7 nm³ carboxy rich domain at the base of the IgG structure allowing binding to an alumina substrate. This results in a domain with a density of 2.70 carboxyl groups per nm³. The surface charge map of the 3D structure of a modified (Glu in place of Gla) Fragment 1 of human Factor II added to the carboxyl terminus of an IgG heavy chain (FIG. 20) shows the concentration of surface charge at the carboxy rich domain that facilitates binding to alumina.

Figure 22:
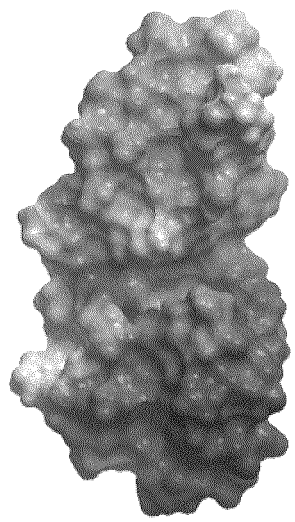
Figure 23:
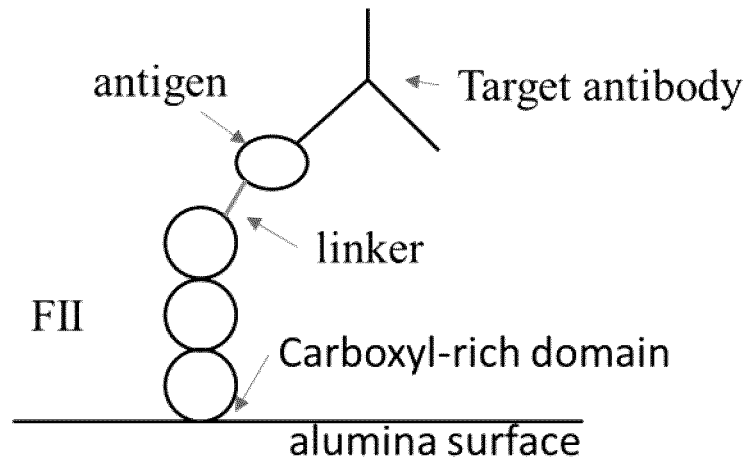
FIG. 23 is a schematic drawing showing an aluminum oxide surface with a prothrombin (FII) interface molecule immobilized to the surface through the Gla (carboxy rich) domain. The FII is modified with a cross linker such as glutaraldehyde for bonding a biomolecule such as an antigen. The antigen is shown bound to its specific antibody. Example 1 is representative of this figure. In Ex. 1, the linker is glutaraldehyde, the antigen is from Influenza B and the target antibody is anti-influenza B virus.
Figure 24:
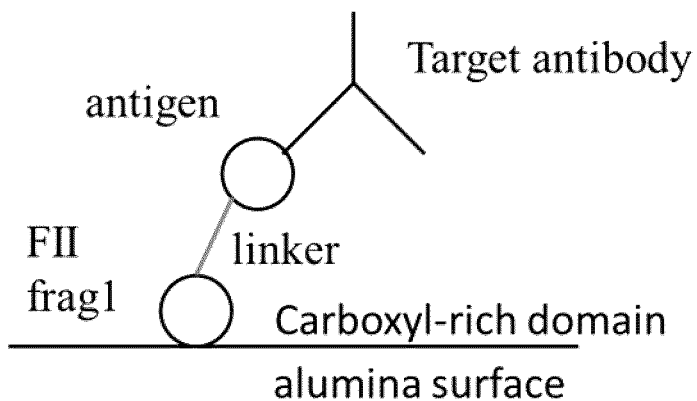
FIG. 24 is a schematic drawing showing an aluminum oxide surface with a Fragment 1 of prothrombin (Frag 1) interface molecule immobilized to the surface through the Gla domain. The Frag 1 is modified with a cross linker for bonding a biomolecule, shown as an antigen, which is bound to its specific antibody. Example 5 is representative of this figure, in which the linker is glutaraldehyde, the antigen is from Hepatitis B virus and the target antibody is anti-Hep B antibody.
Figure 25:
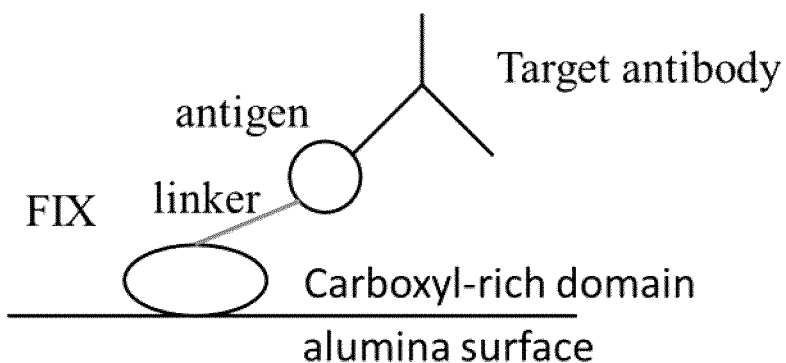
FIG. 25 is a schematic drawing showing an aluminum oxide surface with a Factor IX (FIX) interface molecule immobilized to the surface through the Gla domain. The FIX is modified with a cross linker for bonding a biomolecule, shown as an antigen, which is bound to its specific antibody. For example, the linker can be glutaraldehyde, the immobilized antigen can be influenza B, and the antibody can be anti-influenza B.
Figure 26:
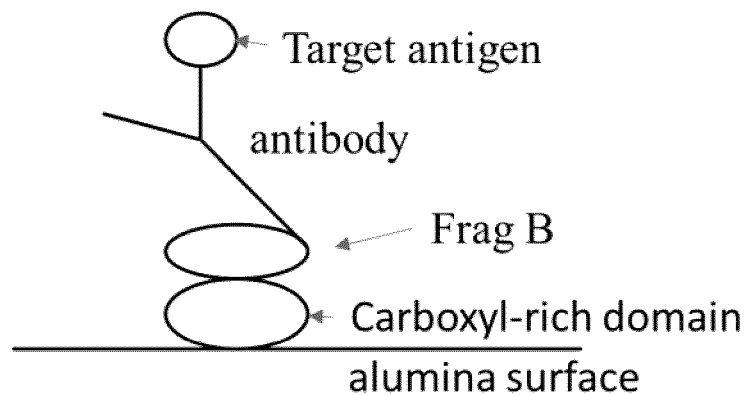
FIG. 26 is a schematic drawing showing an aluminum oxide surface having immobilized thereon, a Fragment B of Protein A engineered to have a Frag 1 of FII incorporated in its structure, such that the Gla domain binds to the aluminum oxide surface. The engineered Fragment B of Protein A provides an interface molecule that is bound to a biomolecule, shown as an antibody, which is bound to its specific antigen. For example, the immobilized antibody can be from anti-influenza B and the antigen can be influenza B.
Figure 27:
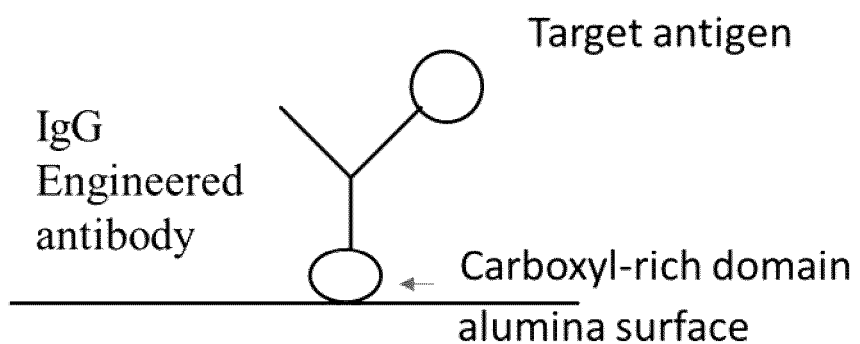
FIG. 27 is a schematic drawing showing an aluminum oxide surface with an antibody (IgG) engineered to have the Gla domain of Fragment 1 of FII incorporated at the carboxyl terminus of its Fc structure, bound to the surface through the Gla domain. The engineered antibody is shown bound to its specific antigen. For example, the Fab can be anti-influenza B and the target antigen can be from influenza B.

The Fragment B domain of Protein A can be linked to the first 32 amino acids of Fragment 1 of human Factor II. There are 10 Gla residues located at sites 6, 7, 14, 16, 19, 20, 25, 26, 29, and 32 on the protein. This forms a 2.2 nm³ carboxy rich domain at the base of the Fragment B structure allowing binding to an alumina substrate. This results in a domain with 9.09 carboxy groups per nm³. The surface charge map of the 3D structure of Fragment B of Protein A linked to the first 32 amino acids of Fragment 1 of human Factor II (FIG. 22) shows the concentration of surface charge at the carboxy rich domain at the base of the Fragment B structure allowing binding to an alumina substrate.

Figure 3:
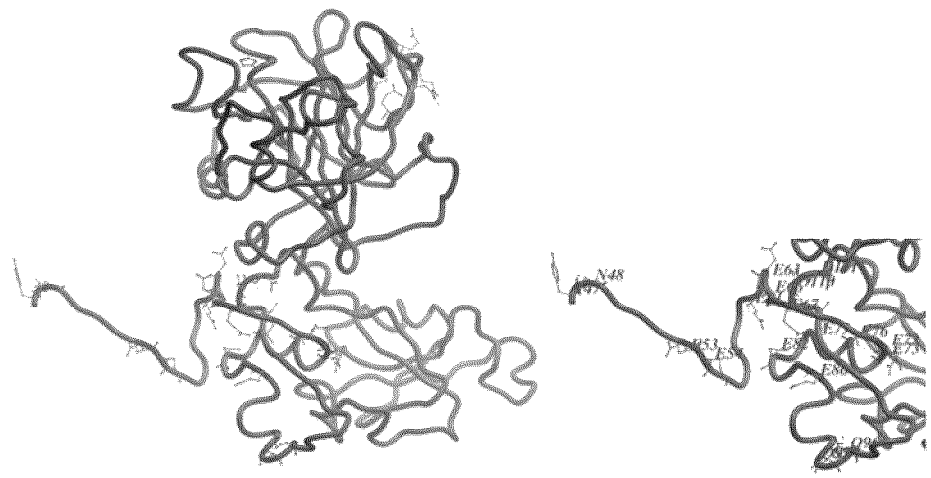
FIG. 3 shows the 3D structure of human coagulation factor IX. There are 12 Gla residues located at sites 7, 8, 15, 17, 20, 21, 26, 27, 30, 33, 36 and 40 on the protein. Additional metal binding sites are 1, 2, 47, 48, 50, 64, 65, 235, 237, 240, 242, and 245 (UnitProt Consortium, 2017b). This forms a 17.0 nm$^3$ carboxyglutamic domain at the base of the structure where binding to the alumina surface occurs.
Figure 4:
FIG. 4 shows the 3D structure of protein S. There are 11 Gla residues located at sites 6, 7, 14, 16, 19, 20, 25, 26, 29, 32 and 36 (UnitProt Consortium, 2017c). This forms a 12.3 nm$^3$ carboxyglutamic domain at the base of the structure where binding to the alumina surface occurs.
Figure 5:
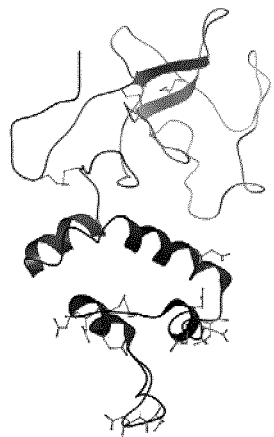
FIG. 5 shows the 3D structure of a modified Fragment 1 of Factor II. There are 10 Asp residues located at sites 6, 7, 14, 16, 19, 20, 25, 26, 29, and 32 on the protein. This forms an 8.7 nm$^3$ carboxy rich domain at the base of the structure where binding to the alumina surface occurs.
Figure 6:
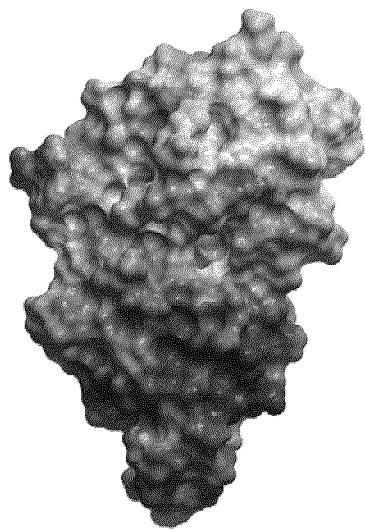
FIG. 6 shows the surface charge map of the 3D structure of a modified Fragment 1 of Factor II. There are 10 Asp residues in place
Figure 7:
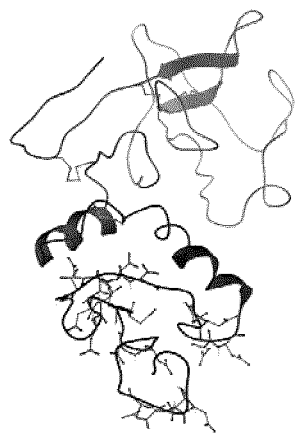
Figure 8:
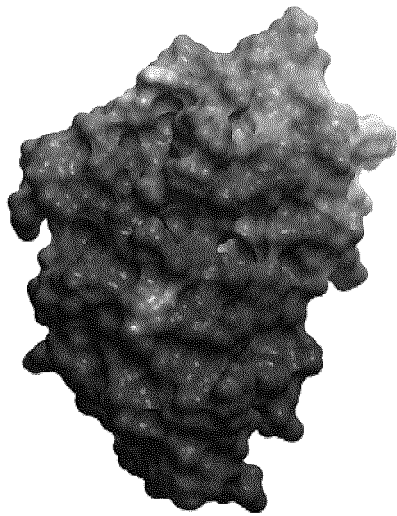

Human factor IX (hFIX) is a vitamin K dependent plasma serine protease that is involved in the intrinsic pathway of blood coagulation. In its pre-pro zymogen form, it consists of 461 amino acids. During biosynthesis to its mature structure, the pre- and pro-peptides are removed. Mature hFIX contains 12 Gla residues near the NH$_2$-terminus, resulting in a Gla rich domain. This region of the protein is a membrane-anchoring domain with affinity to metal ions (Furie & Furie, 1988; 1992; Furie et al., 1979). There are also twelve other metal binding sites that may have an affinity to the alumina substrate surface (UnitProt Consortium, 2017b). FIG. 3 shows the 3-dimensional structure of hFIX. The image identifies the Gla rich domain that has a high affinity to metal. This domain has a volume of 17.0 nm³ and is located at the base of the structure where binding to the alumina substrate occurs. There are 24 carboxyl groups in this domain that gives a density of 1.4 carboxyl groups per nm³.

The binding orientation of hFIX to an alumina substrate is at the Gla domain. At this orientation, the protein has a wide base and so it is structurally stable. This suggests that the binding orientation is be consistent because hFIX proteins are unlikely to shift orientation. This is desirable because a predictable and consistent binding orientation results in consistent properties of the immobilized protein. Factor IX has a molecular weight of 55,000 Da, an isoelectric point in the range of 4.2-4.5, and a dissociation constant of <1.0 μmol/L (Amphlett et al., 1978; Nelsestuen et al., 1978; Thompson, 1986; UnitProt Consortium, 2017b).

Protein S is a glycoprotein that acts as a non-enzymatic cofactor to activated protein C (APC) in the degradation of coagulation factor V/Va and factor VIIIa. It has 11 Gla residues near the $NH_2$-terminal, which are important for membrane binding and are the site of binding onto alumina substrates. Protein S has a molecular weight of 69,000 Da, an isoelectric point in the range of 5.0-5.5 and a dissociation constant is 0.005 μmol/L (Lundwall et al., 1986; Walker, 1981; Sugo et al 1986; UnitProt Consortium, 2017c). FIG. 4 shows the 3-dimensional structure of protein S and the general location of the Gla domain (residues 42-87). The Gla domain is located in near proximity to the $NH_2$-terminal that suggests that it is exposed to the outside of the structure and is the binding site of the protein to the alumina substrate. This forms a 12.3 $nm^3$ carboxyglutamic domain at the base of the structure where binding to the alumina substrate occurs. There are 22 carboxyl groups in the domain that gives a density of 1.79 carboxyl groups per $nm^3$.

TABLE 1

Domain Volume/Density of Free Carboxyl Groups of Interface Molecules

| Protein | Source | Changes | Domain Volume ($nm^3$) | Density ($COOH/nm^3$) |
|---|---|---|---|---|
| FII | natural | none | 8.30 | 2.4 |
| FII-frag1 | natural | none | 8.30 | 2.4 |
| FII-frag1-Asp | synthetic | Asp for Gla | 8.65 | 1.15 |
| FII-frag1-Asp-Asp | synthetic | Asp-Asp for Gla | 7.70 | 2.6 |
| FII-frag1-Asp-Glu | synthetic | Asp-Glu for Gla | 8.50 | 2.35 |
| FII-frag1-Glu-Asp | synthetic | Glu-Asp for Gla | 12.50 | 1.6 |
| FII-fragl-Glu-Glu | synthetic | Glu-Glu for Gla | 11.80 | 1.69 |
| FII-frag1-Bovine | natural | none | 7.00 | 2.86 |
| FII-frag1-IgG-Asp | synthetic | Asp for Gla on IgG | 3.60 | 2.8 |
| FII-frag1-IgG-Glu | synthetic | Glu for Gla on IgG | 3.70 | 2.7 |
| FII-frag1 on Prot. A-fragB | synthetic | Fusion protein | 2.20 | 9.09 |
| FIX | natural | none | 17.00 | 1.40 |
| Protein S | natural | none | 12.30 | 1.79 | ii) Aluminum Oxide Surface

The aluminum oxide surface may take the form of aluminum oxides and hydroxides including calcined aluminas, the various transition aluminas (e.g. gamma, eta, delta), aluminum oxide hydroxides (e.g. boehmite), and amorphous aluminas (e.g. native oxide on aluminum, anodized aluminum and aluminum alloys). In general, binding to the interface molecule occurs at cationic surface sites through ligand exchange with protonated hydroxyl surface groups or through electrostatic attraction between positively charged surface sites, such as exposed aluminum ions, and the polyanionic groups.

The aluminum oxide surface may be formed on a substrate, such as on a particle, powder, magnetic bead, thin film, slide or coating. The aluminum oxide surface may be formed by sputtering, RF sputtering, reactive sputtering, chemical vapour deposition, evaporating, casting, or extruding aluminum metal or an aluminum alloy, and may be further anodized to provide a porous anodized aluminum oxide surface.

iii) Biomolecules

The biomolecule is broadly defined above. For affinity binding assays, the biomolecule may be a member of a binding pair: antibody-antigen, antibody-hapten, enzyme-substrate, enzyme-receptor, hapten-hormone, toxin-receptor, protein-protein, avidin-biotin, aptamer-aptamer target, protein-drug, and drug receptor-drug.

As used herein, the binding partner or bioconjugate of the biomolecule bound to the interface molecule, when used in a diagnostic test for the binding pair, is referred to as an analyte of interest.

In general, binding between binding pairs is referred to as molecular binding. Depending on the binding pairs, the molecular binding may be non-covalent, reversible covalent or irreversible covalent binding. Biomolecules that participate in molecular binding generally include proteins, nucleic acids, carbohydrates, lipids and small organic molecules such as drugs, whether natural, biosynthetic, synthetic or derivatized.

iv) Cross-Linking Agents

The interface molecule, or modified/engineered molecules of the interface molecule with biomolecule, can be activated using any number of homo- or heterobifunctional cross linking agents including: imidoesters, glutaraldehyde, carbodiimides, maleimides, haloacetyles, hydrazides, as well as any others commonly known to those skilled in the art. An example of a homobifunctional cross linking agent is pentane-1,5-dial. An example of a heterobifunctional cross linking agent is 3-[2-pyridyldithio]propionyl hydrazide. The interface can then be bound through the cross linking agent to a biomolecule, such as proteins/peptides, carbohydrates, nucleic acids and lipids. The proteins/peptides, carbohydrates, nucleic acids and lipids thus bound are held at the surface, retain their bioidentity, and remain structurally intact, such that they are recognizable as the original material and will thus interact with antigens, antibodies, aptamers etc. The cross linking agent will vary depending on the chemistries of the interface molecule and the biomolecule, as is well known in the art. A list of common cross linking agents is found in https://tools.thermofisher.com/content/sfs/brochures/1602163-Crosslinking-Reagents-Handbook.pdf.

v) Anodization

Aluminum or anodizable aluminum alloy materials can be used for anodization to create a barrier or porous alumina layer. The main governing factors for the resulting anodic alumina films, include the electrolyte type (Ono, Masuko 2003, Abd-Elnaiem, Gaber 2013), strength (i.e., concentration or pH) (Belwalkar et al. 2008, Araoyinbo et al. 2010, Yim et al. 2007), and temperature (Li, Zhang & Metzger 1998, Abd-Elnaiem, Gaber 2013, Yim et al. 2007) as well as the voltage (Zhu et al. 2011, Ono, Masuko 2003, Belwalkar et al. 2008, Rahman et al. 2012, Abd-Elnaiem, Gaber 2013, Yim et al. 2007). These parameters control the porosity through pore diameter and pore wall thickness (Van Overmeere et al. 2010), along with the dissolution and etch rates of layers. Further treatments during oxidation can include pretreatment (Zhu et al. 2011) and post treatment.

When alumina is soluble in the electrolyte (e.g., oxalic, sulfuric, and phosphoric acids), dissolution of $Al^{3+}$ occurs and a porous alumina layer forms. During the initial period of anodization, a highly resistant $Al_2O_3$ barrier film is created on the aluminum layer. Further anodization results in the propagation of individual paths through the barrier film, which are precursors to pore formation. Next, a breakdown of the barrier film and formation of the porous structure occurs. Once porous oxide formation is complete in the aluminum layer, anodization of an underlying layer occurs (e.g. Ta). When the barrier oxide layer has completely formed current density is approximately zero (Eftekhari 2008).

Of particular interest are porous anodized surfaces formed on a reflective metal for use in a visual assay. The aluminum oxide surface is provided on a reflective metal capable of generating a colour when covered by a porous layer of aluminum oxide. The aluminum oxide surface is anodized, as above, to provide a porous anodized surface, such that, when contacted with a sample to test for analyte specific to the biomolecule, a colour change is detected denoting the presence of the analyte upon binding of the biomolecule and the analyte.

vi) Solvents

Suitable solvents for use in immobilizing the interface molecule on the aluminum oxide surface are typically aqueous solutions, preferably with a low salt content and devoid of anions with a high affinity for the alumina surface (e.g., phosphates, carboxylates, sulfates). Binding time can vary depending on the surface coverage, the solvent, and the pH of the solution.

vii) Signal Amplification

When the aluminum oxide surface is part of a colour generating device, for example for a visual assay, some applications may benefit from signal amplification, that is in providing a bound layer on the device that is sufficient to generate a detectable colour change. For example, if an antibody is attached to, or engineered with, the interface molecule, and the matching antigen is very small (for example less than 1.5 nm), there may not be a significant change in colour upon antigen binding as the change in the film thickness may not be large enough (generally greater than 1.5 nm). To amplify the signal (i.e., detectable colour change), a second antibody can be added to the surface after the surface has been exposed to a sample containing the antigen analyte of interest. The second antibody (specific to the antigen), binds to the antigen bound to the first antibody. This second antibody binding occurs only if the desired antigen is bound to the first antibody, but increases the film thickness, for example by about 7 nm. This increase in thickness results in a dramatic change in interference colours so as to be detectable.

Figure 28:
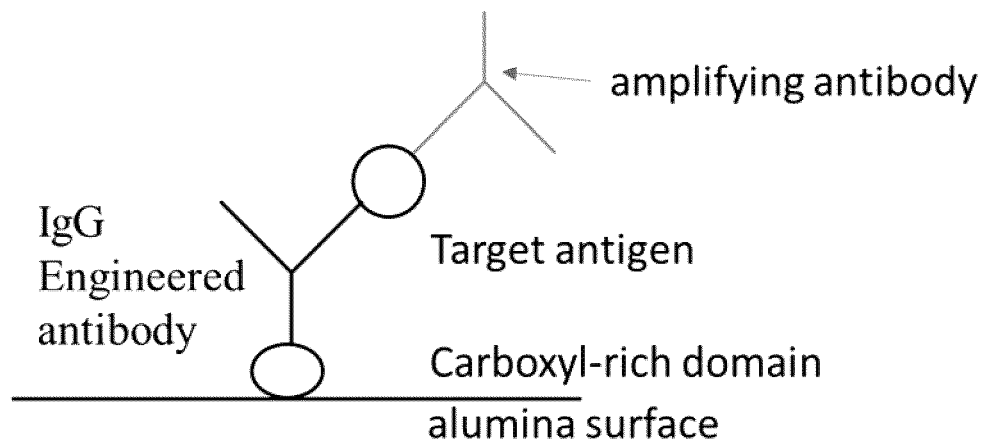
FIG. 28 is a schematic drawing showing an aluminum oxide surface with an antibody (IgG) engineered to have the Gla domain of Fragment 1 of FII incorporated at the carboxyl terminus of its Fc structure, bound to the surface through the Gla domain. The engineered antibody is shown bound to its specific antigen. A second antibody is shown binding to the target antigen, which can be used to amplify the signal. The second antibody may be unmodified or it may be modified with a linked enzyme or radiolabel in order to amplify the signal from the overall device. For example, the Fab may be anti-testosterone, the target antigen can be testosterone, and the amplifying antibody can be anti-testosterone.

One example of signal amplification is depicted in FIG. 28. FIG. 28 shows an aluminum oxide surface as a thin layer of aluminum oxide on an underlying reflective layer, prepared as set out above. An antibody (IgG) is engineered to have the Gla domain of Fragment 1 of FII incorporated at the carboxyl terminus of its Fc structure. The IgG is bound to the aluminum oxide surface through the Gla domain. The engineered antibody is shown bound to its specific antigen. A second antibody is shown binding to the target antigen, which can be used to amplify the signal. The second antibody can be unmodified or it can be modified with a linked enzyme or radiolabel in order to amplify the signal from the overall device.

For example, signal amplification can be used to detect small molecules such as hormone molecules. Testosterone ($C_{19}H_{28}O_2$) has a molecular weight of 288 and a 19 carbon backbone. It is approximately 2 nm in length and less than 1 nm in width, putting it at the lower limit of detection from an interference colour based assay. To amplify the signal a second antibody that recognizes a testosterone-antibody complex can be added to the system. Where ever the testosterone is bound to the antibody, the second antibody binds. This increases the optical path length by about 7-10 nm, which effectively amplifies the signal and allows detection of the hormone of interest.

viii) Kits and Diagnostic Applications

In some embodiments, such as for diagnostic testing, the invention extends to diagnostic systems or kits containing a diagnostic device providing an aluminum oxide surface on an appropriate substrate such as a slide. For visual assays or visual diagnostic devices, the diagnostic device includes an aluminum oxide surface on a reflective metal such as tantalum capable of generating a colour when covered by a porous layer of aluminum oxide. In such applications, the aluminum oxide surface is provided as a porous anodized surface. In some embodiments of a visual assay or visual diagnostic device, the interface molecule is provided on the aluminum oxide surface, and a specific antigen is attached to the interface molecule. Using a specific antigen, this kit detects the presence of an antibody specific to the antigen (analyte) when contacted with a test solution such as a bodily fluid, tissue or the like, since upon binding of the antigen and antibody a visible colour change occurs on the device.

In some embodiments of a visual assay or visual diagnostic device, the kit includes a diagnostic device as set out above, but conjugated with a specific antibody. In some applications, the specific antibody is engineered to include the carboxy rich domain as the interface molecule. This kit allows for the detection of specific antigens in a test solution, since upon binding of the antigen, a visible colour change occurs on the device.

In some embodiments of a visual assay or visual diagnostic device, the kit includes a diagnostic device as set out above, but attached to a bispecific engineered antibody having a first antigenic determinant ($Fab_1$) specific to the interface molecule, and a second antigenic determinant ($Fab_2$) specific to an analyte of interest in a test sample, such as an antigen. This kit allows for the detection of specific antigens in a test solution, since on binding of the antigen to the engineered antibody, a visible colour change occurs. Bispecific antibody synthetic techniques are well known (see for example Brinkmann, Ulrich et al.).

In some embodiments of a visual assay or visual diagnostic device, the kit includes a diagnostic device as set out above, but conjugated with an aptamer. The aptamer binds to its specific target molecule with a visible colour change.

In some embodiments of a visual assay or visual diagnostic device, the kit includes a diagnostic device as set out above, but conjugated to an engineered protein A which includes the carboxy rich domain as the interface molecule. This protein A binds to the FC region of an antibody, ensuring proper orientation of the antibody for detecting its corresponding specific antigen, with a visible colour change.

In some embodiments of a visual assay or visual diagnostic device, the kit includes a diagnostic device as set out above, but the interface molecule is modified or activated by attachment to a cross linking agent. The cross linking agent binds to a specific analyte of interest in a test sample (such as protein in urine) with a visible colour change.

In some embodiments of a visual assay or visual diagnostic device, the kit includes the aluminum oxide surface as set out above, but the interface molecule and the cross linking agent or biomolecule, are provided separately from the aluminum oxide surface, such as by providing one of the following:

a cross linking agent attached, or for attachment to, the interface molecule, the cross linking agent being capable of binding to the analyte of interest; or a biomolecule specific to the analyte of interest, attached to, or for attachment to, the interface molecule; or a biomolecule in the form of an engineered antibody attached to, or for attachment to, the interface molecule through a first antigenic determinant and having a second antigenic determinant specific to the analyte of interest.

The components of the kit can be included separately from the interface molecule for complexing prior to the test, or the interface molecule and the cross linking agent or biomolecule can be formed as a interface complex in the kit. The interface complex is contacted with a sample to test for the analyte, and the sample and the interface complex are then contacted with the aluminum oxide surface. The kit detects the presence of the analyte upon binding of the analyte and the interface complex to the aluminum oxide surface with a detectable colour change.

In addition to the diagnostic device, such kits typically include a container housing the device, and one or more other components. The kit can include pharmaceutical or diagnostic grade components in one or more containers, such as cross linking agents, assay standards, testing components etc. The kit can include instructions or labels promoting or describing the use of the device or components. Instructions can involve written instruction on or associated with packaging of the components. Instructions can also include any oral or electronic instructions provided in any manner, for example for mixing one or more components of the kit, and/or for isolating and analyzing a sample.

To facilitate quantification of distinct analytes in a sample, the assay component can employ standards for the analytes, where the standard is a predetermined amount of an analyte being detected, provided on the device to allow for the quantification of the analyte. Standards can be analyzed to produce working curves equating analyte amounts with the amount of analyte present in the sample. For visual assays, standards can include sample colours charts denoting the diagnostic device pre-testing, for a negative result, and for a positive result.

Techniques for protein printing are well known and can be used to print interface molecules, biomolecules and or complexes of the interface molecule and biomolecule (see for example, Delaney, Joseph T et al., McWilliam I, et al., and Li, J et al.). Protein printing, for example with an ink jet printer can be used to deposit arrays of different proteins to multiplex the tests. Each protein generates a colour that changes if their target molecules (ex. Antibody, antigen, aptamer, DNA strand or RNA strand) are present. For example immunoassays can be multiplexed by placing different proteins on the aluminum oxide surface in a specific pattern. These patterns can be in the form of straight lines, curves, circles, dots, or complex patterns. They provide information on a variety of analytes in the test sample. The results are determined by changes in the colours of various portions of the printed patterns. For example, a variety of antigens can be bound to the diagnostic surface that are characteristic of specific viruses such as those that cause Chikungunya, Dengue Fever, Yellow Fever and Zika. The diagnostic technique identifies not only the disease, but also the serotype present, based upon colour change in specific regions. This multiplexed test determines cases in which a patient has been infected with one or more than one virus or serotype from a single sample.

In some applications, analyte-specific binding to the biomolecule can be detected using any suitable detector, and will depend on the type of test or assay being conducted. In general, the detector includes an illumination source and detection electronics. The light source can be daylight, for example for a point-of-care diagnostic, or other light sources such as LEDs, lasers and filament lamps. These sources can be used in conjunction with optical filters, polarizers, diffraction gratings and other optical components to provide a specified spectral component of light. Other forms of radiation such as bioluminescence, fluorescence, and others can be used. Excitation wavelengths my be in the visible portion of the spectrum (300-700 nm wavelength), or other wavelengths such as infrared and ultraviolet. The absorbed, reflected, or re-emitted light can then be observed and/or detected using the eye (for visible wavelengths), or using photosensitive detectors such as photodiodes or photomulipliers, in combination with spectral and/or spatial filtering.

If colour changes are below the visible detection limit and not detectable by eye, sensitive methods for detection are available. Digital image analysis, spectrophotometric and other photon counting detectors allow for the analysis of shifts in reflected wavelengths. The capture of high resolution images and digital processing is commonly used in biological studies to quantify and analyse colour patterns, so are techniques that are well understood in the art. Quantification of visible colours can be achieved with digital processing. To distinguish colours, plots can be generated using the International Commission on Illumination or Commission Internationale de I'Ecla (CIE) colour space that allows for 2D plots of chromaticity coordinates. Spectrophotometers can provide analysis with full spectrum measurements on reflectance properties, beyond what is detectable by the human eye. For very low levels of light intensity, photon counting detector assemblies (ex. photomultipliers can be used to measure the number of photons by multiplying the signal prior to detection.

One example of a suitable detector is a reflective spectrometer which measures reflectance of reflecting surfaces. Alternatively the detector can be a camera or imaging device. The detection can be at the point-of-care site, such as for a visual assay, or can be remote from the sample collection or patient site.

The methods of the present invention can extend to a computer for data integration, analysis, storage and transmission in order to integrate the detected analyte-specific binding with the data acquired by any on of the data acquisition components. The binding and data thus integrated can then be analyzed and stored by the computer for subsequent access. The computer typically includes an operating system that accesses one or more algorithms and/or software to analyze data from the assay component to determine the presence and/or quantity of analytes that are being tested, for example by comparing to compiled or standard curves. The raw data and/or integrated and analyzed data are displayed on a display screen, such as a computer display or cell phone, PDA and the like.

Figure 36A:
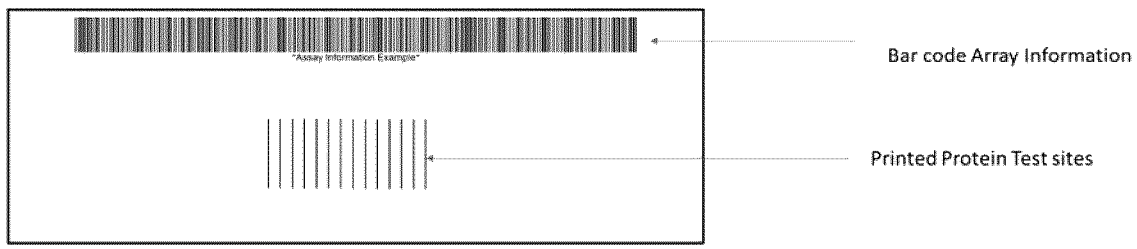
FIGS. 36A and 36B show embodiments of diagnostic devices in accordance with the invention in which test sites are printed in lines or arrays, as set out for FIGS. 35A, 35B, together with barcode or QR codes containing information relating to the array, the assay, the patient etc. for reading by a barcode reader or a smartphone.
Figure 36B:
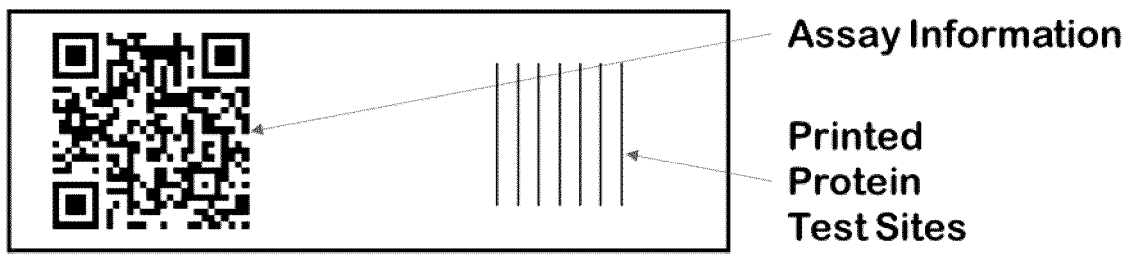

A barcode reader can be provided for automatically entering information about an assay component. The barcode reader can be combined with a barcode activation system which identifies the test to be analyzed and automatically initiates one-point assay calibration of that particular test to reduce user errors. Each individual assay component can contain a unique barcode to be read and used to initialize the apparatus such that the appropriate algorithms are employed. Exemplary embodiments of assay components in accordance with the invention are shown in FIGS. 36A (barcode) and 36B (QR code).

The diagnostic device can be adapted as a sample apparatus, such as a hand held device or kit, including one or more of the components such as described above.

ix) Applications

The aluminum oxide surface on which an interface providing carboxy rich domain is immobilized in accordance with this invention has far reaching applications, including for example: protein coatings on various surfaces for a variety of products such as in biomedical applications; coatings on anodic thin films for medical diagnostic devices as visual immunoassays, coatings on anodic thin films for environmental monitoring; coatings on anodic thin films for food safety diagnostic devices; coatings on anodic films in microtitre plates for ELISA testing and the like; coatings on MEMS/NEMS for diagnostics, coatings on nanoparticles for targeted therapeutic delivery; coatings on nanoparticles for contrast imaging; alumina particles for column based affinity separation applications; magnetic particles for affinity recovery of biomolecules and cells; research assay to verify veracity of antibodies before testing; coatings for plastic sample cups and lids to facilitate testing, and coating on medical devices or implants.

The present invention is also illustrated by the following non-limiting examples.

EXAMPLES (i) Aluminum Oxide Surfaces and Interface Molecules as Affinity Device

Example 1

This example demonstrates the bonding of a protein (specifically a viral antigen) to an alumina substrate on which prothrombin is immobilized as an interface molecule. Alumina substrates were made by first sputtering tantalum to a thickness of 200 nm onto an amorphous support, followed by sputtering aluminum to a thickness of 120 nm on the Ta. Aluminum was converted to alumina through electrochemical oxidation (anodization) which was carried out using phosphoric acid anodization at 8V with an electrolyte of 0.4 M phosphoric acid until the current decayed to near 0 mA. This produced a layer of $Al_2O_3$ with a thickness of approximately 190 nm on top of a $Ta_2O_5$ layer of thickness 14 nm. The colour of the resulting device, when observed through a polarizer with white light at 15°, was gold. Prothrombin was placed on the alumina surface (10 µL of a 1 mg/mL solution) for 30 minutes in a 100% RH environment and then rinsed thoroughly with deionized water. After allowing the device to air dry the colour had changed to rust. The device was then immersed in a 0.5% (v/v) glutaraldehyde solution with a 25 mM phosphate buffer at pH of 6.9 for 60 minutes. Following another rinse with deionized water, an antigen for the Influenza B virus (10 µL of a 1.75 mg/mL solution), strain Hong Kong 5/72, was placed on the surface for 60 minutes. The device was then rinsed in a 25 mM phosphate buffer for 60 minutes and allowed to air dry, upon which the colour had shifted to lavender. The shift in colour was caused by the increase in optical path length which resulted from the immobilization of the antigen.

Example 2

This example illustrates that proteins such as IgG do not bind to the anodic alumina surface. Devices were made as in example 1 and prothrombin was immobilized on the surface in two of three delineated spots with the same procedure as described in Example 1. A rust colour was observed after immobilization of prothrombin. Antiprothrombin was added to one spot with prothrombin and the remaining blank spot for 15 minutes (10 µL of a 100 µg/mL solution) and rinsed off with deionized water. The device was allowed to air dry and then observed at 15°, as in Example 1. A burgundy spot was observed on the spot that contained both the antigen (prothrombin) and the protein antibody (antiprothrombin). The colour shift indicated that the proteins immobilized were recognized by the antibody which bound to them and changed the overall thickness of the protein layer. There was no observable colour shift on the bare anodic oxide surface that had antiprothrombin added to it. This indicates that there was not enough residual protein on the surface to alter the optical path length of the light, so the protein did not bind to the anodic surface.

Example 3

This example shows how an immobilized protein can be made specific by capping the glutaraldehyde with an amino protein, specifically tris(hydroxymethyl)aminomethane), such than no bonding occurs with the immobilized prothrombin.

A device was made, prothrombin was immobilized on the surface, and a glutaraldehyde solution was added, as described in Example 1. The device was then submersed in a 1×TBS buffer to cap all glutaraldehyde open for binding. A layer of protein (specifically an IgG antibody, goat raised anti-influenza B) was placed on the surface for 30 minutes and then rinsed off with deionized water. The device was allowed to air dry and then was observed at 15°. There was no visible colour change noticed. This lack of colour change indicated that the optical path length was not altered by the exposure to the nonspecific antibody that was added. This is important to show that the device functions as an affinity substrate without false positives from non-specific proteins.

Example 4

This example illustrates a visual assay for an antibody-antigen complex on the surface by binding the antigen to a prothrombin interface. Devices were made, prothrombin was immobilized on the surface, and the cross-linker was added as described in Example 1. A synthetic surface antigen for Hepatitis B (Hep B) was then bonded to the prothrombin using the same procedure as in Example 1. A rust colour was observed after bonding of the antigen.

The remaining glutaraldehyde was then capped with a 0.1M L-lysine solution in 0.3M phosphate buffer of pH 7.0 for 60 minutes. Finally, serum samples (n=20) were placed on the surface for 15 minutes and rinsed off with deionized water. The device was allowed to air dry and then observed at 15° where a magenta spot was observed. The colour shift indicated that the bonded proteins were recognized by the antibody which bound to them and changed the overall thickness of the protein layer.

The above examples use the naturally occurring protein prothrombin as an interface coating on alumina. Prothrombin was then activated with a homo- or hetero-bifunctional molecule to link the protein of interest to the prothrombin. If a shorter interface molecule than prothrombin (~10 nm) is desired, (e.g. ~3 nm) then Fragment 1 of the prothrombin molecule can be used in place of prothrombin, as shown in the examples below. Glutaraldehyde or any other homo- or hetero-bifunctional molecule can then be used to link biomolecules of interest to the Fragment 1.

Example 5

This example illustrates the ability to form an antibody-antigen complex on the surface by binding the antigen to Fragment 1 of FII. Devices were made as in Example 1, and Fragment 1 was immobilized on the alumina surface instead of prothrombin. Fragment 1 was placed on the device surface (10 μL of a 0.3 mg/mL solution) for 30 minutes in a 100% RH environment and then rinsed thoroughly with deionized water. After allowing the device to air dry the colour had changed to light rust. An antigen to the Hepatitis B virus was then bonded on the surface using the same cross-linking procedure as in Example 1. A rust colour was observed after immobilization of the Hepatitis B antigen.

The remaining glutaraldehyde was then capped with a 0.1M L-lysine solution in 0.3M phosphate buffer of pH 7.0 for 60 minutes. Finally, the anti-Hep B antibody was placed on the surface for 15 minutes (10 μL of a 100 μg/mL solution) and rinsed off with deionized water. The device was allowed to air dry and then observed at 15° where a purple spot was observed. The colour shift indicated that the proteins immobilized were recognized by the antibody which bound to them and changed the overall thickness of the protein layer.

Example 6

This example illustrates an interface molecule immobilized on a aluminum oxide surface and activated by attaching the interface molecule to a cross linking agent, for use in binding to an analyte in a test sample. Devices were made as in Example 1 and prothrombin was immobilized on the aluminum oxide surface in two spots. On one spot, the prothrombin was activated by attaching a glutaraldehyde cross linking agent, as described in Example 1. The other spot was not modified. Both spots were rust coloured. A solution of nonsense IgG (i.e., not specific for prothrombin) was added to both spots and allowed to sit for 60 minutes followed by a washing step and air drying. The spot containing the activated prothrombin bound the nonsense IgG, as indicated by a colour change to purple. The second spot did not change colour indicating that no binding occurred. This example is schematically illustrated in FIG. 31, and is illustrative of an application of a diagnostic test to detect protein in urine, as a point of care device.

(ii) Engineered Biomolecules with Carboxy Rich Interface

Example 7

This example illustrates an interface molecule engineered as an anchor protein with a carboxy rich amino acid sequence for binding to the alumina surface. Here, the first 32 amino acids from Fragment 1 from human Factor II are modified and coupled directly to an aluminum oxide surfaces in a stable form. The modified Fragment 1 is bound to the alumina surface through the cluster of carboxyl groups associated with the dicarboxyl amino acid Asp. Gla residues located at sites 6, 7, 14, 16, 19, 20, 25, 26, 29, and 32 on the protein are substituted for with Asp. This halves the number of carboxylic groups available for binding to the surface relative to native Fragment 1 in Example 6. This substitution results in a carboxy rich domain at the amino terminus of Fragment 1 as shown in the computer model of the structure (FIG. 5), generated by protein folding software. The sequence listing for the modified Gla domain of the F1 fragment is provided in SEQ ID NO. 4. The computer model of the surface charge on the protein (FIG. 6) supports this, showing the carboxy rich domain at the base of the engineered interface molecule where binding to the alumina substrate occurs.

Example 8

This example illustrates an interface molecule engineered as an anchor protein with a carboxy rich amino acid sequence for binding to the alumina surface. Here, the first 32 amino acids from Fragment 1 from human Factor II are modified and coupled directly to an aluminum oxide surfaces in a stable form. The modified Fragment 1 is bound to the alumina surface through the cluster of carboxyl groups associated with the dicarboxyl amino acids Asp (a dicarboxylic amino acid). Gla residues located at sites 6, 7, 14, 16, 19, 20, 25, 26, 29, and 32 on the protein are substituted for with Asp-Asp. This retains the number of carboxylic groups available for binding to the surface relative to native Fragment 1 in Example 6. This substitution results in a carboxy rich domain at the amino terminus of Fragment 1 as shown in the computer model of the structure (FIG. 7). The sequence listing for the modified Gla domain of the F1 fragment is provided in SEQ ID NO. 5. The computer model of the surface charge on the protein (FIG. 8) supports this, showing the carboxy rich domain at the base of the engineered interface molecule.

Example 9

This example illustrates an interface molecule engineered with a carboxy rich amino acid sequence for binding to the alumina surface. The first 32 amino acids from Fragment 1 from human Factor II are modified for direct coupling to an aluminum oxide surface in a stable form. The modified Fragment 1 is bound to the alumina surface through the cluster of carboxyl groups associated with the dicarboxyl amino acids Asp-Glu. Gla residues located at sites 6, 7, 14, 16, 19, 20, 25, 26, 29, and 32 on the protein are substituted for with Asp-Glu. This retains the number of carboxylic groups available for binding to the surface relative to native Fragment 1 in Example 6. This substitution results in a carboxy rich domain at the amino terminus of Fragment 1 as shown in the computer model of the structure (FIG. 9). The sequence listing for the modified Gla domain of the F1 fragment is provided in SEQ ID NO. 6. The computer model of the surface charge on the protein (FIG. 10) supports this, showing the carboxy rich domain at the base of the engineered interface molecule.

Example 10

This example illustrates an engineered interface molecule, in which the first 32 amino acids from Fragment 1 from human Factor II are modified for coupling directly to an aluminum oxide surfaces in a stable form. The modified Fragment 1 is bound to the alumina surface through the cluster of carboxyl groups associated with the dicarboxyl amino acids Glu-Asp. Gla residues located at sites 6, 7, 14, 16, 19, 20, 25, 26, 29, and 32 on the protein are substituted for with Glu-Asp. This retains the number of carboxylic groups available for binding to the alumina surface relative to native Fragment 1 in Example 6. This substitution results in a carboxy rich domain at the amino terminus of Fragment 1 as shown in the computer model of the structure (FIG. 11). The sequence listing for the modified Gla domain of the F1 fragment is provided in SEQ ID NO. 7. The computer model of the surface charge on the protein (FIG. 12) supports this, showing the carboxy rich domain at the base of the engineered interface molecule.

Example 11

This example illustrates a further engineered interface molecule. The first 32 amino acids from Fragment 1 from human Factor II are modified for coupling directly to an aluminum oxide surfaces in a stable form. The modified Fragment 1 is bound to the alumina surface through the cluster of carboxyl groups associated with the dicarboxyl amino acids Glu-Glu. Gla residues located at sites 6, 7, 14, 16, 19, 20, 25, 26, 29, and 32 on the protein are substituted for with Glu-Glu. This retains the number of carboxylic groups available for binding to the surface relative to native Fragment 1 in Example 6. This substitution results in a carboxy rich domain at the amino terminus of Fragment 1 as shown in the computer model of the structure (FIG. 13). The sequence listing for the modified Gla domain of the F1 fragment is provided in SEQ ID NO. 8. The computer model of the surface charge on the protein (FIG. 14) supports this, showing a carboxy rich domain at the base of the engineered molecule.

Example 12

This example illustrates an interface molecule from Fragment 1 from bovine Factor II. Bovine Fragment 1 has an insertion of an extra amino acid at position 4 relative to human Fragment 1. The use of bovine Fragment 1 results in a carboxy rich domain at the amino terminus of Fragment 1 as shown in the computer model of the structure (FIG. 15). The sequence listing for the modified Gla domain of the F1 fragment is provided in SEQ ID NO. 9. The computer model of the surface charge on the protein (FIG. 16) supports this, showing the carboxy rich domain at the base of the molecule.

(iii) Genetically Engineered or Chemically Derivatized Protein/Antibody with Carboxy Rich Domain

Example 13

This example illustrates an antibody (here an IgG heavy chain) that is chemically altered or engineered with a carboxy rich amino acid sequence from Fragment 1 of human Factor II, for coupling directly to an aluminum oxide surface in a stable form. This engineered molecule is bound or incorporated into the carboxyl terminus of the Fc fragment of the antibody. Gla located at sites 6, 7, 14, 16, 19, 20, 25, 26, 29, and 32 on the protein are substituted for with Asp. This halves the number of carboxylic groups available for binding to the surface relative to natural Fragment 1. This substitution results in a carboxy rich domain at the amino terminus of modified Fragment 1 as shown in the computer model of the structure (FIG. 17). The sequence listing for the modified Gla domain of the F1 fragment is provided in SEQ ID NO. 10. The computer model of the surface charge on the protein (FIG. 18) supports this, showing a carboxy rich domain at the base of the engineered molecule for binding to alumina.

Example 14

This example illustrates an IgG heavy chain antibody chemically altered or engineered with a carboxy rich amino acid sequence from Fragment 1 of human Factor II, for coupling directly to an aluminum oxide surfaces in a stable form. The engineered molecule is bound or incorporated into the carboxyl terminus of the Fc fragment of an antibody. Gla residues located at sites 6, 7, 14, 16, 19, 20, 25, 26, 29, and 32 on the protein are substituted for with Glu, which halves the number of carboxylic groups available for binding to the surface relative to natural Fragment 1. This substitution results in a carboxy rich domain at the amino terminus of Fragment 1 as shown in the computer model of the structure (FIG. 19). The sequence listing for the modified Gla domain of the F1 fragment with the heavy chain IgG antibody is provided in SEQ ID NO. 11. The computer model of the surface charge on the protein (FIG. 20) supports this, showing a carboxy rich domain at the base of the engineered molecule for binding to the alumina surface.

Example 15

Figure 21:
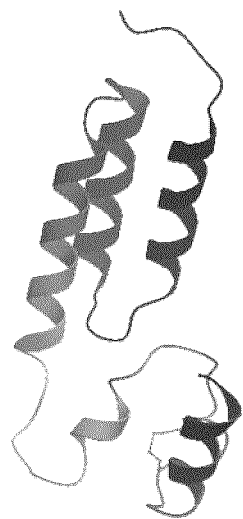

This example illustrates another engineered interface-biomolecule. The Fragment B domain of Protein A is linked to the first 32 amino acids of Fragment 1 of human Factor II. There are 10 Gla residues located at sites 6, 7, 14, 16, 19, 20, 25, 26, 29, and 32 on the Fragment 1 protein. The engineered molecule is shown in FIG. 21, as generated in the computer model. The sequence listing for the engineered molecule is provided in SEQ ID NO. 12. This provides a 2.2 nm$^3$ carboxy rich domain at the base of the Fragment 1-Fragment B structure, allowing binding to an alumina substrate. This results in a carboxy rich domain with 9.09 carboxy groups per nm$^3$. The surface charge map of the 3D structure of Fragment B of Protein A linked to the first 32 amino acids of Fragment 1 of human Factor II (FIG. 22) shows the concentration of surface charge at the base of the engineered molecule for binding to the alumina substrate.

Example 16

Gla sequences containing one or more of the Gla domain from Factor II, Factor VII, Factor X, Factor II with a Kringle domain, Protein C, Protein Z, and a synthetic peptide sequence having a carboxy rich domain (see U.S. Pat. No. 9,694,048 to Bauzon et al.), were cloned onto each of the Fc fragments of an IgG (anti Gaussia luciferase). The cloning techniques used were standard Fc engineering techniques at the Centre for the Commercialization of Antibodies and Biologics at the University of Toronto. (Liu et al.). The Gla domains from these proteins or from the synthetic peptide were cloned as units from 1 to 3, such that one, two or three Gla domains from the protein were present on each of the Fc fragments of the IgG biomolecule. These are designated as Gla1x, Gla 2x or Gla 3x in Table 2. The cloning techniques used a flexible linker sequence (Gly-Gly-Gly-Gly-Ser, as shown in SEQ ID NO. 20) and an Open Reading Frame (SEQ ID NO. 21) to attach the Gla domain to the Fc fragment. The flexible linker sequence was also used to link the Gla domains when more than one was attached per heavy chain of the Fc fragment. Other linkers and ORF are well known in the art and may be used. The cloning technique used subclone 4275 hG1, where hG1 refers to the Ab isotype that is expressed as (i.e. human IgG1), and 4275 is the antibody that specifically binds to Gaussia luciferase and is used as the standard negative control for this mammalian in vivo work (Liu et al.). The cloning added the Gla sequence to the carboxyl terminus of both heavy chains of the Fc fragment. Thus, a Gla1x, as listed in Table 2 had two Gla domains, a Gla2x had 4 Gla domains, and a Gla3x had 6 Gla domains cloned on the Fc fragment of the IgG. All clones were expressed in 10 ml volumes. These expressed forms utilized the native form of the Gla domain sequence in each case.

TABLE 2

| Source of GLA | SEQ ID NO. |
| --- | --- |
| Factor VII Gla1x | SEQ ID NO. 16 |
| Factor VII Gla2x | SEQ ID NO. 16 |
| Factor VII Gla3x | SEQ ID NO. 16 |
| Factor X Gla1x | SEQ ID NO. 13 |
| Protein C Gla1x | SEQ ID NO. 15 |
| Protein C Gla2x | SEQ ID NO. 15 |
| Protein C Gla3x | SEQ ID NO. 15 |
| Factor II Gla1x | SEQ ID NO. 14 |
| Factor II Gla3x | SEQ ID NO. 14 |
| Factor II Gla with Kringle 1x | SEQ ID NO. 19 |
| Factor II Gla with Kringle 2x | SEQ ID NO. 19 |
| Synthetic Peptide Gla 1x | SEQ ID NO. 18 |
| Synthetic Peptide Gla2x | SEQ ID NO. 18 |
| Synthetic Peptide Gla3x | SEQ ID NO. 18 |
| Protein Z Gla1x | SEQ ID NO. 17 |
| Protein Z Gla2x | SEQ ID NO. 17 |
| Protein Z Gla3x | SEQ ID NO. 17 |

Example 17

This example illustrates the strong colour shifts that resulted with immobilizing engineered antibodies from Example 16 on a range of initial aluminum sputtered thicknesses. The thin film device was formed by sputtering a tantalum layer 200 nm thick onto substrates, followed by sputtering an aluminum layer ranging between 90 to 140 nm thick. The thin metallic films were then anodized in a mixed electrolyte containing 0.4 M phosphoric acid and 0.1 M oxalic acid with an applied constant potential of 4 V. Upon removal from the electrolyte bath the surface was thoroughly rinsed with distilled water. The device surface was subsequently exposed to protein solutions of native prothrombin (0.004 mg) and recombinant IgGs modified with Gla domains on the Fc region, as described in Example 16 (Table 2). Proteins were exposed for 30 minutes, after which the solution was removed, rinsed with distilled water and air dried. Regardless of the alumina thickness, the engineered IgGs (Gla 1x) (~150 kDa) generated a strong colour shift on the device surface when viewed at 75 degrees from normal as did the native prothrombin. As the number of cloned Gla units increased from 1-3, the ability to generate a colour shift declined such that, for the Gla3x engineered antibodies, the colour shift was only slightly visible to the human eye, although other detection techniques may be used, as indicated above. These colour changes indicate that engineered proteins can be successfully immobilized to tailored alumina thicknesses and generate varying colour shifts within the first and second order colour regions.

Example 18

This example illustrates that the engineered antibodies of Example 16 were immobilized to surface through the Gla modification of Example 16, while the IgG molecules on their own did not lead to a visible colour shift. Surfaces coated with engineered human antibodies of Example 16 were subsequently coated with a solution of either goat anti-human (GAH) IgG (0.02 mg) or goat anti-mouse (GAM) IgG (0.02 mg). When GAH IgG (pos. control) was exposed to the spot with immobilized engineered antibody an increase in the colour shift resulted, whereas when GAM IgG (neg. control) was exposed to the spot with immobilized engineered human antibody no visible colour shift resulted. Both GAH and GAM solutions were also exposed to the bare device surface for 30 minutes and no colour shift resulted from either solution. This clearly demonstrated a colour shift due to the formation of a secondary IgG layer when GAH detected the adsorbed recombinant antibody on the surface.

Example 19

This example illustrates the strong colour shifts that resulted when the immobilized engineered antibodies of Example 16 were exposed to their specific antigen, Gaussia luciferase. The thin film devices were formed by sputtering a tantalum layer 200 nm thick onto silicon substrates, followed by sputtering an aluminum layer that was 110 nm thick. The thin metallic films were then anodized in a mixed electrolyte containing 0.4 M phosphoric acid and 0.1 M oxalic acid with an applied constant potential of 4 V. Upon removal from the electrolyte bath the surface was thoroughly rinsed with distilled water. The device surface was subsequently exposed to protein solutions of native prothrombin (0.004 mg) and a recombinant IgG (anti-Gaussia luciferase) modified with Gla domains (Factor VII Gla1x) on the Fc region as described in Example 16. Proteins were exposed for 30 minutes, after which the solution was removed, rinsed with distilled water and air-dried. The engineered IgGs (~150 kDa) generated a strong colour shift (light purple) on the device surface when viewed at 75 degrees from normal as did the native prothrombin. The surfaces were then exposed to a 0.2 mg/ml solution of Fragment 1 from prothrombin (Factor II) to cap any active sites on the surface. No further colour change was observed after rinsing in distilled water and drying. Solutions of Gaussia luciferase (0.2 mg/ml) or procalcitonin (0.2 mg/ml) were then exposed to the surface for 30 minutes followed by a rinse and drying. The surfaces with the engineered IgG that were exposed to Gaussia luciferase changed to violet while the surfaces exposed to procalcitonin did not change colour. The prothrombin treated surfaces did not change colour with either Gaussia luciferase or procalcitonin. These colour changes indicate that engineered proteins can be successfully immobilized to alumina surfaces and generate colour shifts when exposed to their specific antigens. The engineered and immobilized antibodies retain their functionality.

INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention can be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, a size range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

Abd-Elnaiem, A. & Gaber, A. 2013, "Parametric study on the anodization of pure aluminum thin film used in fabricating nano-pores template", International Journal of Electrochemical Science, vol. 8, no. 7, pp. 9741-9751.

Amphlett, G. W., Byrne, R., & Castellino, F. J. (1978). The binding of metal ions to bovine factor IX. The Journal of Biological Chemistry, 253(19), 6774-6779.

Araoyinbo, A. O., Ahmad Fauzi, M. N., Sreekantan, S. & Aziz, A. 2010, "A novel process to produce nanoporous aluminum oxide using titration technique to prepare the neutral electrolyte", Journal of Non-Crystalline Solids, vol. 356, no. 20-22, pp. 1057-1060.

Bajaj, S. P., Butkowski, R. J., & Mann, K. G. (1975). Prothrombin fragments. Ca2+ binding and activation kinetics. The Journal of Biological Chemistry, 250(6), 2150-2156.

Belwalkar, A., Grasing, E., Van Geertruyden, W., Huang, Z. & Misiolek, W. Z. 2008, Effect of processing parameters on pore structure and thickness of anodic aluminum oxide (AAO) tubular membranes.

Bowen, W. R., & Gan, Q. (1992). Properties of Microfiltration Membranes: The Effects of Adsorption and Shear on the Recovery of an Enzyme. Biotechnology and Bioengineering, 40, 491-497.

Brinkmann, U., Kontermann, R., The making of bispecific antibodies. MABS 2017, 9, 2, 182-212 http://dx.doe.org/10.1080/19420862.2016.1268307.

Eftekhari, A. 2008, Nanostructured materials in electrochemistry, Weinheim: Wiley-VCH, Chichester.

Furie, B., & Furie, B. C. (1988). The molecular basis of blood coagulation. Cell, 53(4), 505-518.

Furie, B. C., Blumenstein, M., & Furie, B. (1979). Metal binding sites of a gamma-carboxyglutamic acid-rich fragment of bovine prothrombin. The Journal of Biological Chemistry, 254(24), 12521-12530.

Delaney, J., Smith, P., Schubert U., Inkjet printing of proteins, SoftMater, 2009, 5, 4866-4877. DOI:10.1039/b909878j.

Kotkow, K. J., Furie, B., & Furie, B. C. (1993). The interaction of prothrombin with phospholipid membranes is independent of either kringle domain. The Journal of Biological Chemistry, 268(21), 15633-15639.

Li, F., Zhang, L. & Metzger, R. M. 1998, "On the growth of highly ordered pores in anodized aluminum oxide", Chemistry of Materials, vol. 10, no. 9, pp. 2470-2480.

Li, J., Rossignol, F., and Macdonald, J. Inkjet printing for biosensor fabrication; combining chemistry and technology for advanced manufacturing, Lab Chip, 2015, 15, 2538-2558 DOI: 10.1039/c51c00235d.

H. Liu, A. Saxena, S. S. Sidhu, and D. Wu, Fc Engineering for Developing Therapeutic Bispecific Antibodies and Novel Scaffolds, Front Immunol. 2017; 8: 38.

Lundwall, Å, Dackowski, W., Cohen, E., Shaffer, M., Mahr, A., Dahlbäck, B., et al. (1986). Isolation and sequence of the cDNA for human protein S, a regulator of blood coagulation. Proceedings of the National Academy of Sciences of the United States of America, 83(18), 6716-6720.

Mann, K. G. (1976). Prothrombin. Methods Enzymol, 45(pt. B), 123-156.

McWilliam I., Chong Kwan M., Hall D., Inkjet printing for the production of protein microarrays. Methods Mol Biol. 2011; 785:345-51 DOI:10.1007/978-1-61779-286-1_23.

Murray, J. P. (1980). Physical Chemistry of Virus Adsorption and Degradation on Inorganic Surfaces: Its relation to wastewater treatment. Cincinnati, OH: United States Environmental Protection Agency.

Murray, J. P., & Laband, S. J. (1979). Degradation of Poliovirus by Adsorption on Inorganic Surfaces. Applied and Environmental Microbiology, 37(3), 480-486.

Nelsestuen, G. L., Kisiel, W., & Di Scipio, R. G. (1978). Interaction of vitamin K dependent proteins with membranes. Biochemistry, 17(11), 2134-2138.

Ono, S. & Masuko, N. 2003, "Evaluation of pore diameter of anodic porous films formed on aluminum", Surface and Coatings Technology, vol. 169-170, pp. 139-142.

Rahman, M. M., Garcia-Caurel, E., Santos, A., Marsal, L. F., Pallarès, J. & Ferré-Borrull, J. 2012, "Effect of the anodization voltage on the pore-widening rate of nanoporous anodic alumina", Nanoscale Research Letters, vol. 7, no. 1, pp. 474-474.

Sugo, T., Dahlbäck, B., Holmgren, A., & Stenflo, J. (1986). Calcium binding of bovine protein S. effect of thrombin cleavage and removal of the gamma-carboxyglutamic acid-containing region. The Journal of Biological Chemistry, 261(11), 5116-5120.

Thompson, A. R. (1986). Structure, function, and molecular defects of factor IX. Blood, 67(3), 565-572.

Thurman, R. B., & Gerba, C. P. (1988). Characterization of the effect of aluminum metal on poliovirus. Journal of Industrial Microbiology, 3, 33-38.

UnitProt Consortium. (2017a). UniProtKB-P00734 (thrb_human). Retrieved Feb. 4, 2017, from http://www.uniprot.org/uniprot/P00734

UnitProt Consortium. (2017b). UniProtKB-P00740 (fa9_human). Retrieved Apr. 4, 2017, from http://www.uniprot.org/uniprot/P00740

UnitProt Consortium. (2017c). UniProtKB-P07225 (pros_human). Retrieved Mar. 18, 2017, from http://www.uniprot.org/uniprot/P07225

Van Overmeere, Q., Blaffart, F. & Proost, J. 2010, "What controls the pore spacing in porous anodic oxides?", Electrochemistry Communications, vol. 12, no. 9, pp. 1174-1176.

Walker, F. J. (1981). Regulation of activated protein C by protein S. the role of phospholipid in factor va inactivation. The Journal of Biological Chemistry, 256(21), 11128-11131.

Walz DA, Hewett-Emmett D, Seegers W H. (1977). Amino acid sequence of human prothrombin fragments 1 and 2. Proceedings of the National Academy of Sciences of the United States of America, 74(5), 1969.

Wefers, K., & Misra, C. (1987). Oxides and Hydroxides of Aluminum: Alcoa Technical Paper No. 19, Revised. Alcoa Laboratories.

Yim, S., Bonhôte, C., Lille, J. & Wu, T. 2007, "Parameter effects for the growth of thin porous anodic aluminum oxides", ECS Transactions, vol. 6, no. 8, pp. 267-274.

Zhu, Z., Garcia-Gancedo, L., Qiang, L., Flewitt, A., Milne, W. I. & Moussy, F. 2011, "Size-tunable porous anodic alumina nano-structure for biosensing", Soft Nanoscience Letters, vol. 1, no. 3, pp. 55-60.

The invention claimed is:

1. A diagnostic system or a kit for testing whether binding has occurred to an analyte of interest, comprising:
   an aluminum oxide surface;
   an interface molecule comprising a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is capable of being immobilized to the aluminum oxide surface; and
   one of:
   i) a cross linking agent attached to the interface molecule for binding to the analyte;
   ii) a biomolecule attached to the interface molecule through one or more covalent bonds, the biomolecule being specific to the analyte;
   iii) a biomolecule in the form of an engineered antibody attached to the interface molecule through a first antigenic determinant specific to the interface molecule, and having a second antigenic determinant specific to the analyte; and
   iv) a biomolecule in the form of an engineered antibody attached to the interface molecule though an Fc fragment of the antibody and having Fab fragments specific to the analyte, and wherein:
   the interface molecule and one of (i), (ii), (iii) and (iv) are immobilized to the aluminum oxide surface; or
   the interface molecule and one of (i), (ii), (iii) and (iv) are provided as an interface complex for contact with the analyte prior to immobilizing to the aluminum oxide surface,
   such that, when contacted with a sample to test for the analyte, the presence of the analyte is detected upon binding of the analyte either to the cross linking agent if (i) is present, or to the biomolecule if (ii), (iii) or (iv) is present.

2. The diagnostic system or kit of claim 1, wherein
   the aluminum oxide surface is provided on a reflective metal capable of generating a colour when covered by a porous layer of aluminum oxide; and
   the aluminum oxide surface is a porous anodized surface; such that, when contacted with a sample to test for the analyte, a colour change is detected denoting the presence of the analyte upon binding of the analyte either to the cross linking agent if (i) is present, or to the biomolecule if (ii), (iii) or (iv) is present.

3. A method of testing whether binding has occurred to an analyte of interest, comprising:
   a) providing an aluminum oxide surface;
   b) providing an interface molecule capable of binding to the aluminum oxide surface, the interface molecule comprising a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is capable of being immobilized to the aluminum oxide surface, and wherein the interface molecule is attached to one of:
   i) a cross linking agent for binding to the analyte;
   ii) a biomolecule specific to an analyte;
   iii) a biomolecule in the form of an engineered antibody having a first antigenic determinant specific to the interface molecule, and having a second antigenic determinant specific to the analyte of interest; and
   iv) a biomolecule in the form of an engineered antibody attached to the interface molecule though an Fc fragment of the antibody and having Fab fragments specific to the analyte of interest;
   c) either immobilizing the interface molecule and one of (i), (ii), (iii) and (iv) on the aluminum oxide surface, or forming an interface complex of the interface molecule with one of (i), (ii), (iii) and (iv);
   d) contacting the surface of c) or the interface complex of c) with a sample to test for the analyte; and
   e) detecting the presence of the analyte either upon binding of the analyte to the surface of c), or upon binding of the analyte and the interface complex to the aluminum oxide surface.

4. The method of claim 3, wherein:
the aluminum oxide surface is provided on a reflective metal capable of generating a colour when covered by a porous layer of aluminum oxide; and
the aluminum oxide surface is a porous anodized surface; such that, when contacted with a sample to test for the analyte, a colour change is detected denoting the presence of the analyte upon binding of the analyte either to the cross linking agent if (i) is present, or to the biomolecule if (ii), (iii), or (iv) is present.

5. The diagnostic system or kit of claim 2, wherein the carboxy rich domain provides:
at least 10 free carboxyl groups within a molecular volume of 2.2-25 nm$^3$; or
at least 20 free carboxyl groups within a molecular volume of 2.2-25 nm$^3$; or
at least 10 free carboxyl groups within a molecular volume of 2.2-17 nm$^3$, or
at least 20 free carboxyl groups within a molecular volume of 2.2-17 nm$^3$; or
at least 10 free carboxyl groups within a molecular volume of 7.0-17 nm$^3$, or
at least 20 free carboxyl groups within a molecular volume of 7.0-17 nm$^3$.

6. The diagnostic system or kit of claim 5, wherein:
the cross linking agent is covalently bonded to the interface molecule; or
the biomolecule is covalently bonded to the interface molecule through a cross-linking agent; or
the interface molecule and the biomolecule are engineered as an amino acid sequence such that the interface molecule and biomolecule are attached through peptide bonds; or
the interface molecule is an engineered or synthetic protein, polypeptide or antibody incorporating the carboxy rich domain; or
the biomolecule is an engineered antibody having a first antigenic determinant specific to the interface molecule, and having a second antigenic determinant specific to the analyte of interest; or
the biomolecule is an engineered antibody attached to the interface molecule though an Fc fragment of the antibody and having Fab fragments specific to the analyte of interest.

7. The diagnostic system or kit of claim 5, wherein the interface molecule is provided on the aluminum oxide surface as a continuous or discontinuous coating, as delineated spots or lines, or as an array.

8. The diagnostic system or kit of claim 5 comprising a plurality of interface molecules, the plurality of the interface molecules comprising different types and being spaced on the aluminum oxide surface with the biomolecule attached to one type of the plurality of the interface molecules, or with a specific biomolecule attached to each type of the plurality of the interface molecules such that different specific biomolecules are attached.

9. The diagnostic system or kit of claim 5, wherein the aluminum oxide surface is provided on a substrate in the form of a particle, powder, thin film, slide, strip, filter, bead, magnetic bead, magnetic particle, or coating.

10. The diagnostic system or kit of claim 5, wherein:
the aluminum oxide surface is provided by sputtering, evaporating, casting or extruding aluminum metal or an aluminum alloy, which is further anodized to provide a porous anodized aluminum oxide surface; or
the aluminum oxide surface is provided by RF sputtering, reactive sputtering or chemical vapour depositing aluminum oxide onto a substrate.

11. The diagnostic system or kit of claim 5, wherein the interface molecule or the interface complex is immobilized as a coating on the aluminum oxide surface from a solution of the interface molecule in a suitable solvent, followed by removing the solution.

12. The diagnostic system or kit of claim 5, wherein the interface molecule includes one or more of the amino acids selected from the group consisting of aspartic acid (Asp), glutamic acid (Glu), and gamma-carboxyglutamic acid (Gla).

13. The diagnostic system or kit of claim 5, wherein the interface molecule is a Vitamin K dependent protein, a fragment thereof containing a Gla domain, or a fragment thereof containing a modified Gla domain in which one or more of the Gla residues are substituted with Glu, Asp, Glu-Glu, Glu-Asp, Asp-Glu, or Asp-Asp.

14. The diagnostic system or kit of claim 5, wherein the interface molecule and the biomolecule are formed as an engineered molecule such that the carboxy rich domain is included in a protein, a polypeptide, an antigen, an antibody, a carbohydrate, an aptamer or a lipid.

15. The diagnostic system or kit of claim 14, wherein the carboxy rich domain includes one or more Gla domains of a Vitamin K dependent protein, or a fragment thereof containing the one or more Gla domains, and the engineered molecule includes protein A, fragment B of protein A, or an IgG molecule.

16. The diagnostic system or kit of claim 5, wherein the interface molecule is a protein, one or more Gla domains of a protein, or a modified Gla domain of a protein in which one or more of the Gla residues are substituted with Glu, Asp, Glu-Glu, Glu-Asp, Asp-Glu, or Asp-Asp, wherein the protein is selected from the group consisting of prothrombin, Fragment 1 of prothrombin, protein S, coagulation Factor IX, Factor X, Factor VII, protein C, matrix Gla protein, and bone Gla protein.

17. The diagnostic system or kit of claim 5, wherein the interface molecule is a protein, one or more Gla domains of a protein, or a modified Gla domain of a protein in which one or more of the Gla residues are substituted with Glu, Asp, Glu-Glu, Glu-Asp, Asp-Glu, or Asp-Asp, wherein the protein is selected from the group consisting of prothrombin, Fragment 1 of prothrombin, protein S, and coagulation Factor IX.

18. The diagnostic system or kit of claim 5, wherein the biomolecule is a member of a binding pair selected from the group consisting of antibody-antigen, antibody-hapten, enzyme-substrate, enzyme-receptor, toxin-receptor, protein-protein, avidin-biotin, aptamer-aptamer target, and drug receptor-drug.

19. The diagnostic system or kit of claim 5, wherein the interface molecule and the biomolecule are in the form an interface complex of an engineered antibody attached to the interface molecule through an Fc fragment of the antibody and having Fab fragments specific to the analyte; and the interface complex includes one or more of the carboxy rich domains cloned to the carboxy terminus of each heavy chain of the Fc fragment of the antibody.

20. The diagnostic system or kit of claim 19, wherein the one or more of the carboxy rich domains includes one or more Gla domains of a Vitamin K dependent protein, a fragment thereof containing a Gla domain, or a fragment thereof containing a modified Gla domain in which one or more of the Gla residues are substituted with Glu, Asp, Glu-Glu, Glu-Asp, Asp-Glu, or Asp-Asp.

21. The diagnostic system or kit of claim 20, wherein the antibody is an IgG, the protein is selected from Factor II, Factor VII, Factor X, protein C, protein Z, and the interface complex includes one or two of the Gla domains attached to each of the heavy chains of the Fc fragment.

22. A diagnostic system or a kit for testing whether binding has occurred to an analyte of interest, comprising:
- an aluminum oxide surface;
- an interface molecule comprising a polypeptide having at least one carboxy rich domain providing at least 5 free carboxyl groups within a molecular volume of 2.2-25 nm$^3$, the free carboxyl groups being provided by amino acids containing two or more carboxyl groups, through which the interface molecule is capable of being immobilized to the aluminum oxide surface; and
- a biomolecule attached to the interface molecule for specific binding to the analyte;
- wherein the interface molecule and the biomolecule are immobilized to the aluminum oxide surface; or the interface molecule and the biomolecule are provided as an interface complex for contact with the analyte prior to immobilizing to the aluminum oxide surface,
- such that, when contacted with a sample to test for the analyte, the presence of the analyte is detected upon binding of the analyte either to the cross linking agent if i) is present, or to the biomolecule if ii), iii) or iv) is present.

* * * * *

UNITED STATES PATENT AND TRADEMARK OFFICE
CERTIFICATE OF CORRECTION

| | | |
|---|---|---|
| PATENT NO. | : 12,061,195 B2 | Page 1 of 1 |
| APPLICATION NO. | : 16/971284 | |
| DATED | : August 13, 2024 | |
| INVENTOR(S) | : Robert Edward Burrell | |

It is certified that error appears in the above-identified patent and that said Letters Patent is hereby corrected as shown below:

In the Claims

In Column 72, in Claim 19, Line 61, please delete "domains cloned to" and replace with -- domains attached to --.

Signed and Sealed this
Second Day of September, 2025

Coke Morgan Stewart
*Acting Director of the United States Patent and Trademark Office*